US008293536B2

(12) United States Patent
Mori et al.

(10) Patent No.: US 8,293,536 B2
(45) Date of Patent: Oct. 23, 2012

(54) REAGENT, REAGENT KIT AND ANALYZING METHOD

(75) Inventors: Yusuke Mori, Hyogo (JP); Hiroki Takeshita, Hyogo (JP)

(73) Assignee: Sysmex Corporation, Kobe-shi (JP)

( * ) Notice: Subject to any disclaimer, the term of this patent is extended or adjusted under 35 U.S.C. 154(b) by 0 days.

(21) Appl. No.: 12/753,565

(22) Filed: Apr. 2, 2010

(65) Prior Publication Data

US 2010/0255591 A1 Oct. 7, 2010

Related U.S. Application Data

(62) Division of application No. 11/923,259, filed on Oct. 24, 2007, now abandoned.

(30) Foreign Application Priority Data

Oct. 30, 2006 (JP) .................. 2006-294504
Oct. 30, 2006 (JP) .................. 2006-294525

(51) Int. Cl.
*G01N 33/52* (2006.01)
*G01N 33/50* (2006.01)
*G01N 33/48* (2006.01)
*G01N 33/00* (2006.01)

(52) U.S. Cl. ................... 436/63; 436/10; 436/8; 436/17
(58) Field of Classification Search .................. 436/10, 436/8, 17, 63
See application file for complete search history.

(56) References Cited

U.S. PATENT DOCUMENTS

| | | | |
|---|---|---|---|
| 3,884,579 A | 5/1975 | Mauthner | |
| 4,103,041 A | 7/1978 | Macho et al. | |
| 4,336,029 A | 6/1982 | Natale | |
| 4,882,284 A | 11/1989 | Kirchanski et al. | |
| 4,981,803 A | 1/1991 | Kuroda | |
| 5,691,204 A | 11/1997 | Kim et al. | |
| 5,891,731 A | 4/1999 | Akai et al. | |
| 6,114,173 A | 9/2000 | Zelmanovic et al. | |
| 6,689,391 B2 | 2/2004 | Goswami et al. | |
| 6,835,431 B1 | 12/2004 | Alperovich et al. | |
| 2002/0034825 A1 | 3/2002 | Schweigart | |
| 2003/0219850 A1 | 11/2003 | Tsuji et al. | |
| 2005/0031540 A1 | 2/2005 | Nielsen | |

(Continued)

FOREIGN PATENT DOCUMENTS

EP 1 136 563 A2 9/2001

(Continued)

OTHER PUBLICATIONS

Cohen P. et al., Quantification of Human Platelet Inositides and the Influence of Ionic Environment of Their Incorporation of Orthophosphate 32P, 1971, The Journal of Clinical Investigation, vol. 50, pp. 762-772.*

(Continued)

*Primary Examiner* — Christine T Mui
(74) *Attorney, Agent, or Firm* — Sughrue Mion, PLLC

(57) ABSTRACT

A method for analyzing platelet is described. In the method, a measurement sample is prepared by mixing a sample and a dye for staining platelet. The dye is selected from the group consisting of Capri blue, Nile blue and brilliant cresyl blue. By irradiating cells in the measurement sample with light, scattered light and fluorescence emitted from the cells is measured. The platelet is detected on the basis of the scattered light and the fluorescence.

A reagent kite and a reagent are also described.

8 Claims, 21 Drawing Sheets

| | Dye | Concentration | Structure | Scattergram (1) | Scattergram (2) | Results |
|---|---|---|---|---|---|---|
| Example 1 | Capri blue GON | 0.4ppm | 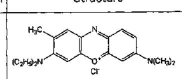 | | | Good staining of platelet |
| Example 2 | Nile blue chloride | 0.4ppm | 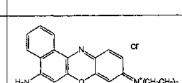 | | | Good staining of platelet |
| Example 3 | Brilliant cresyl blue ALD | 1ppm | 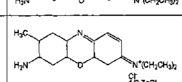 | | | Good staining of platelet |
| Comparative Example 1 | Azure A | 2ppm | 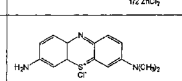 | | | Poor staining of platelet |
| Comparative Example 2 | Azure B | 2ppm | 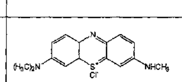 | | | Poor staining of platelet |

U.S. PATENT DOCUMENTS

2008/0102526 A1  5/2008  Mori et al.

FOREIGN PATENT DOCUMENTS

| EP | 1 918 709 A1 | 5/2008 |
|---|---|---|
| WO | 99/24527 A1 | 5/1999 |

OTHER PUBLICATIONS

"Platelet Counting by the RBC/Platelet Ratio Method", Coagulation and Transfusion Medicine / Reference Method for Platelet Counting, American Journal of Clinical Pathologists, 2001, pp. 460-464, vol. 115.

Morgenstern E, et al.; "Lipids as a cytochemical substrate for the binding of basic dyes in blood-, epithel- and tumor cells", Histochemie, ; vol. 10, No. 4; Jan. 1, 1967; pp. 309-320.

Ostle A. G. et al.; "Nile Blue A As A Fluorescent Stain for Poly-Beta Hydroxy Butyrate", Applied and Environmental Microbiology, vol. 44, No. 1, 1982, pp. 238-241.

Spiekermann, Patricia et al.; "A sensitive, viable-colony staining method using Nile red for direct screening of bacteria that accumulate polyhydroxyalkanoic acids and ther lipid storage compounds", vol. 171, No. 2. Jan. 1999, pp. 73-80.

\* cited by examiner

Fig. 1A

| | Dye | Concentration | Structure | Scattergram (1) | Scattergram (2) | Results |
|---|---|---|---|---|---|---|
| Example 1 | Capri blue GON | 0.4ppm | 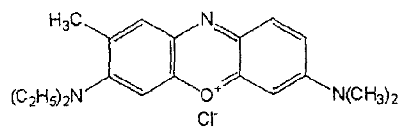 | | | Good staining of platelet |
| Example 2 | Nile blue chloride | 0.4ppm | 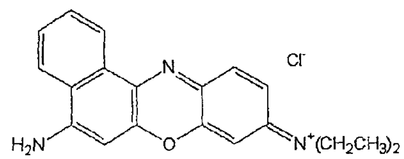 | | | Good staining of platelet |
| Example 3 | Brilliant cresyl blue ALD | 1ppm | 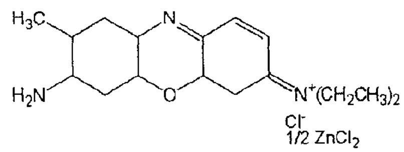 | | | Good staining of platelet |
| Comparative Example 1 | Azure A | 2ppm | 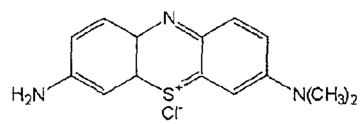 | | | Poor staining of platelet |
| Comparative Example 2 | Azure B | 2ppm | 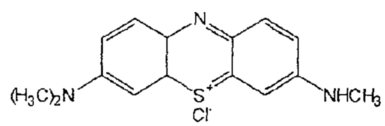 | | | Poor staining of platelet |

Fig. 1B

| | Dye | Concentration | Structure | Scattergram (1) Scattergram (2) | Results |
|---|---|---|---|---|---|
| Comparative Example 3 | Azure C | 2ppm | 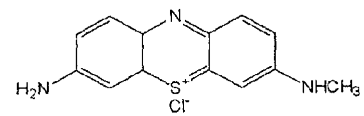 | | Poor staining of platelet |
| Comparative Example 4 | Methylene blue NNX | 2ppm | 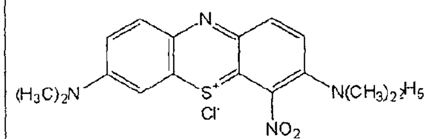 | | Poor staining of platelet |
| Comparative Example 5 | Cresyl violet acetate | 20ppm | 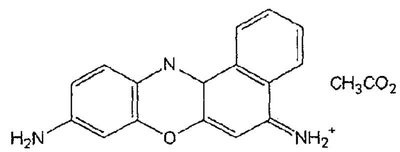 | | Not stained |
| Comparative Example 6 | Basic Green 5 | 20ppm | 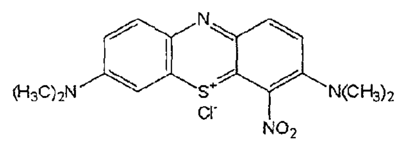 | | Poor staining of platelet |
| Comparative Example 7 | Methylene blue | 2ppm | 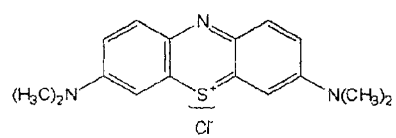 | | Poor staining of platelet |

Fig. 1C

| | Dye | Concentration | Structure | Scattergram (1) | Scattergram (2) | Results |
|---|---|---|---|---|---|---|
| Comparative Example 8 | New Methylene Blue | 20ppm | 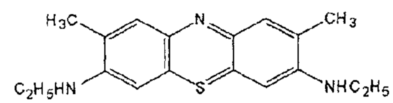 | | | Poor staining of platelet |
| Comparative Example 9 | Toluidine blue N | 2ppm | 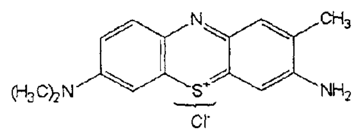 | | | Poor staining of platelet |
| Comparative Example 10 | Oxazine 750 | 2ppm | 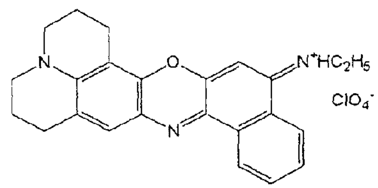 | | | Poor staining of platelet |
| Comparative Example 11 | Oxazine 1 | 20ppm | 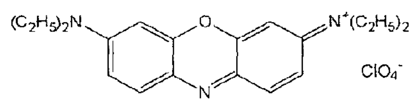 | | | Not stained |
| Comparative Example 12 | Oxazine 4 | 20ppm | 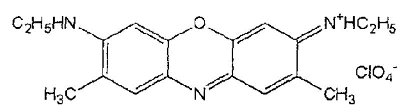 | | | Not stained |

REAGENT, REAGENT KIT AND ANALYZING METHOD

CROSS REFERENCE

This is a divisional of application Ser. No. 11/923,259, filed Oct. 24, 2007 which claims benefit of JP 2006-294504, filed Oct. 30, 2006 and JP 2006-294525 filed Oct. 30, 2006. The entire disclosures of the prior applications are considered part of the disclosure of the accompanying divisional application and are hereby incorporated by reference.

BACKGROUND OF THE INVENTION

1. Field of the Invention

The present invention relates to a reagent, a reagent kit and a method for analyzing platelets. The present invention also relates to a reagent, a reagent kid and a method for analyzing platelets and reticulocytes.

2. Description of the Related Art

Human blood contains various blood cells such as red blood cells, white blood cells and platelets. Among these, platelets are anucleate cells of 2 to 3 µm in diameter. In normal human blood, there are 150,000 to 350,000 platelets per µl.

However, it is known that the number of platelets in blood is decreased upon affection with thrombocytopenia such as idiopathic thrombocytopenic purpura (ITP) or with acute leukemia. It is generally judged that blood transfusion is necessary when the number of platelets in blood is lower than 10000 per µl. Accordingly, rapid and accurate measurement of the number of platelets is important in the clinical field.

One of known methods of measuring platelets is a method of utilizing electrical resistance. This method is a method which involves measuring a pulse of electrical impedance upon passage of a platelet-containing sample between 2 electrodes and analyzing it in a histogram. In the method of utilizing electrical resistance, however, there is a problem that sufficient measurement accuracy cannot be achieved depending on a sample.

Consequently, a method of measuring the number of platelets by using a labeled antibody specific for surface antigen of platelet is known (see American Journal of Clinical Pathologists (2001):115, pp. 460-464). It is known that the method described in this literature is a highly sensitive method, but that the method generally requires a long time until results are obtained because an antigen-antibody reaction is used in measurement. Accordingly, this method is not suitable as a method of measuring platelets in the clinical field requiring, for example, urgent judgment of whether blood transfusion is required or not.

Reticulocytes are also contained in blood. Reticulocytes are young red blood cells just after release of denucleated erythroblastic cells in bone marrow into peripheral blood. Reticulocytes are characterized in that as traces in the cell maturation process, a small amount of RNA and organelles such as ribosome and mitochondria, which are not contained in mature red blood cells, are contained in their cells.

In the filed of clinical examination, classification and counting of reticulocytes is very important for grasping hematopoiesis in bone marrow in a patient. In a healthy subject with normal myelopoiesis, reticulocytes account for 0.5 to 3.0% of all red blood cells. On the other hand, the number of reticulocytes is decreased in an abnormal state of myelopoiesis (for example, in a suppressed state of myelopoiesis) or increased in an accelerated state of myelopoiesis. Specifically, reticulocytes are decreased during a plastic anemia and chemical therapy for malignant tumor or increased in hemolytic anemia etc.

A method of rapidly measuring cells in blood (that is, blood cells such as white blood cells, reticulocytes and red blood cells) by using the principle of flow cytometry is known. As such measurement method, a method of counting and identifying reticulocytes, red blood cells and platelets in a sample of whole blood, as well as a reagent composition for use in the method, is disclosed in U.S. Pat. No. 6,114,173. In the method, a reagent mixture containing a cationic dye (particularly oxazine 750) is mixed with a sample containing reticulocytes. Then, the scattered light and absorption light of the resulting mixture are measured by flow cytometry. By using the measured scattered light and f absorption light as parameters, reticulocytes are counted and distinguished from red blood cells and platelets.

U.S. Pat. No. 4,882,284 discloses a method of discriminating white blood cells from red blood cells and platelets in whole blood not lysed. In the method, a reagent containing a fluorescent dye which absorbs red light is contacted with whole blood not lysed. It is described therein that an oxazine dye used as the fluorescent dye which absorbs red light stains white blood cells, and thus the white blood cells can be distinguished from red blood cells and platelets by measurement using flow cytometry.

U.S. Pat. No. 5,891,731 discloses a reagent for measurement of reticulocytes, which comprises at least one dye specifically staining reticulocytes and a dye specifically staining white blood cells. This patent also describes that an oxazine-based dye can specifically stain white blood cells.

Fragmented red blood cells, lipid and the like may appear in blood. In measurement of platelets, fragmented red blood cells, lipid and the like are similar in size to platelets and are thus known as contaminants to influence the measurement. The influence of these contaminants is significant particularly in measurement of a sample in which the number of platelets is so low that blood transfusion is necessary. However, the above-mentioned literatures do not describe that platelets are measured more accurately by suppressing the influence of such contaminants.

From the foregoing, there is demand for techniques capable of measuring platelets by distinguishing them more clearly from other blood cells and contaminants in blood such as lipid particles.

SUMMARY OF THE INVENTION

The scope of the present invention is defined solely by the appended claims, and is not affected to any degree by the statements within this summary.

The present invention provides a method capable of analyzing platelet by discriminating them more clearly from other blood cells and contaminants in blood such as lipid particles in an analysis method using flow cytometry.

A first aspect of the present invention is a method for analyzing platelet, comprising the steps of: preparing a measurement sample by mixing a sample and a dye for staining platelet, the dye being selected from the group consisting of Capri blue, Nile blue and brilliant cresyl blue; measuring scattered light and fluorescence emitted from cells in the measurement sample by irradiating the cells with light; and detecting platelet on the basis of the scattered light and the fluorescence.

A second aspect of the present invention is a reagent kit for analyzing platelet, comprising: a first reagent containing a buffer; and a second reagent containing a dye for staining platelet, wherein the dye is selected from the group consisting of Capri blue, Nile blue and brilliant cresyl blue.

A third aspect of the present invention is a reagent for analyzing platelet by flow cytometer, comprising a dye for staining platelet, wherein the dye is selected from the group consisting of Capri blue, Nile blue and brilliant cresyl blue.

DESCRIPTION OF THE DRAWINGS

FIGS. 1A to C show scattergrams obtained by measurement using a regent containing a different oxazine dye.

DESCRIPTION OF THE PREFERRED EMBODIMENTS

Figure 2:
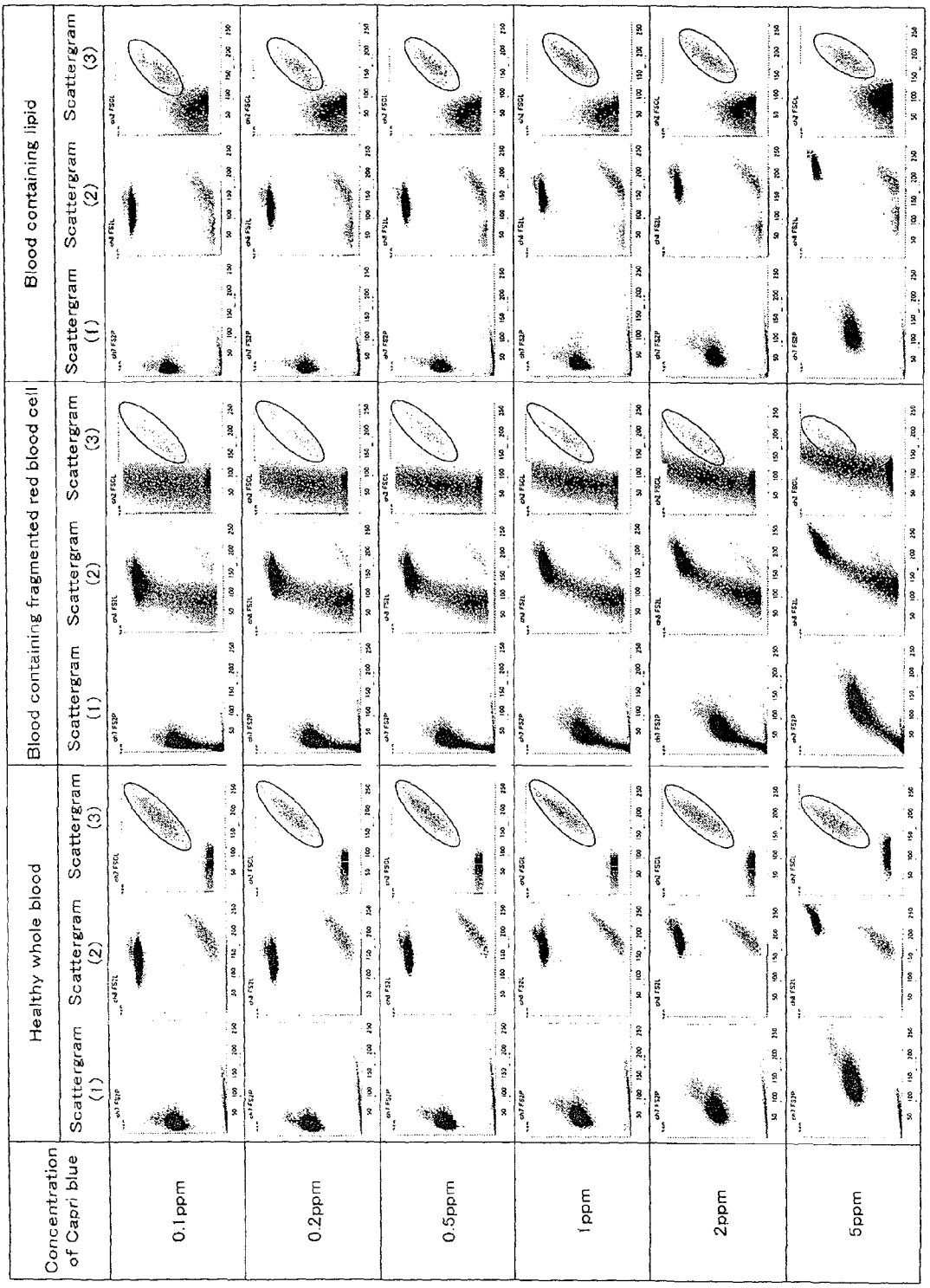
FIG. 2 shows scattergrams obtained by measurement using each reagent for analyzing platelet with different concentrations of Capri blue.

For obtaining a platelet measurement reagent capable of measuring platelets by discriminating them more clearly from other blood cells and contaminants in blood such as lipid particles in an measurement method using flow cytometry, the inventors made extensive study with 100 or more dyes. As a result, they found that a specific oxazine dye can specifically stain platelets, and the present invention was thereby completed. It has not been known that the specific oxazine dye found now to be usable for staining platelets can specifically stain platelets to such a degree that platelets can be distinguished from contaminants such as lipid particles. This oxazine dye can fluorescence-stain platelets. Platelets stained with this oxazine dye can emit strong fluorescence in measurement by flow cytometry. The platelets can thereby be distinguished from contaminants.

In this specification, the "contaminants" in blood refer to components in blood which can prevent accurate measurement of platelet. Such contaminants include lipid particles, fragmented red blood cells and the like contained in blood.

The reagent for analyzing platelet (hereinafter referred to sometimes as PLT reagent) in one embodiment of the invention comprises a dye for staining platelet. The dye is capable of specifically staining platelet. The dye is at least one oxazine dye selected from the group consisting of Capri blue, Nile blue and brilliant cresyl blue. The dye is preferably a dye capable of staining platelet so as to make it distinguishable from lipid particles. By using the PLT reagent containing the dye, platelets even in a sample containing contaminants capable of preventing detection of platelets can be measured rapidly with higher accuracy by preventing the influence of such contaminants and other blood cells in blood.

Capri blue includes, for example, Capri blue GON represented by the following formula (II):

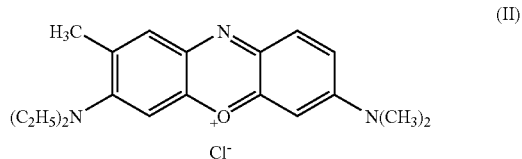

(II)

Nile blue includes, for example, Nile blue represented by the following formula (III):

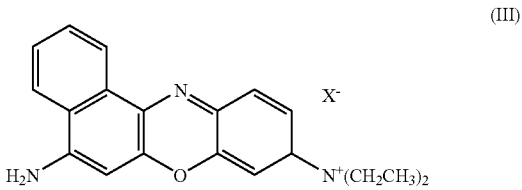

(III)

wherein $X^-$ is $Cl^-$ or $\frac{1}{2}SO_4^{2-}$.

Brilliant cresyl blue includes, for example, brilliant cresyl blue ALD represented by the following formula (IV):

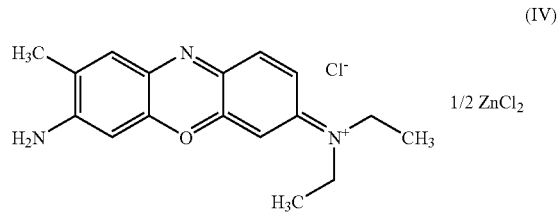

(IV)

The above-mentioned dyes for staining platelet are commercially available. For example, Capri blue GON is available from Chroma Gesellshaft Schmid & Co., Nile blue from Tokyo Chemical Industry Co., Ltd. and Sigma-Aldrich respectively, and brilliant cresyl blue ALD from Sigma-Aldrich.

The above-mentioned dyes can stain platelets to such an extent that the platelets can be distinguished from fragmented red blood cells.

It was also found that a reagent containing a dye capable of specifically staining reticulocyte and the above dye for staining platelet can be used to distinguish reticulocytes and platelets more clearly from other blood cells and contaminants in blood. From the foregoing, a reagent for analyzing reticulocyte and platelet (hereinafter referred to sometimes as RET/PLT reagent) containing a first dye for staining platelet and a second dye for staining reticulocyte can be mentioned as another embodiment of the invention.

The above dye for staining platelet can be used as the first dye contained in the RET/PLT reagent.

The second dye contained in the RET/PLT reagent may be a dye capable of staining reticulocyte to such a degree as to be distinguishable from other blood cells or contaminants. The second dye is preferably a cyanine dye capable of staining a nucleic acid (hereinafter referred to sometimes as nucleic acid-staining cyanine dye). The nucleic acid-staining cyanine dye may be a conventionally known dye. Examples of such dye can include dyes disclosed in U.S. Pat. No. 5,891,731, dyes disclosed in WO 98/26007, dyes disclosed in WO 01/086264 and dyes disclosed in U.S. Pat. No. 4,957,870. Preferable among these dyes are those represented by the following formula (I):

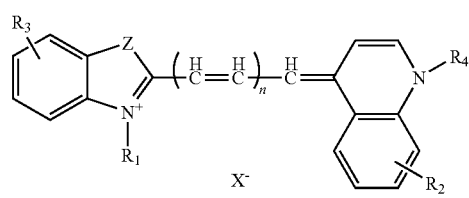

wherein $R_1$ represents a hydrogen atom, a C1 to C6 alkyl group, or —$CH_2(CHR_5)_xOR_6$; $R_2$ and $R_3$ independently represent a hydrogen atom, a halogen atom, a cyano group, a C1 to C6 alkyl group, a C1 to C6 alkoxy group, an aryl group, or an aralkyl group; $R_4$ represents a C1 to C6 alkyl group, —$CH_2$ $(CHR_7)_yOR_8$, an aryl group, or an aralkyl group; $R_5$ and $R_7$ independently represent a hydrogen atom or a C1 to C3 hydroxyalkyl group; $R_6$ and $R_8$ independently represent a hydrogen atom, an acyl group, or a C1 to C3 alkyl group; Z represents a sulfur atom, an oxygen atom, a selenium atom, or $CR_9R_{10}$; $R_9$ and $R_{10}$ independently represent a C1 to C3 alkyl group; n is an integer of 1 or 2; x and y independently represent an integer of 0 to 3; and $X^-$ is an anion.

The C1 to C6 alkyl group represented by $R_1$ in the formula (I) may be either linear or branched. The C1 to C6 alkyl group represented by $R_1$ includes, for example, a methyl group, ethyl group, propyl group, butyl group, isobutyl group, sec-butyl group, tert-butyl group, pentyl group and hexyl group. Among these groups, a methyl or ethyl group is preferable.

The group represented by each of $R_2$ and $R_3$ in the formula (I) may be substituted at any of the ortho-, meta- and para-positions. The C1 to C6 alkyl group represented by each of $R_2$ and $R_3$ can include the same groups as described above. The C1 to C6 alkoxy group can include a methoxy group, ethoxy group, propoxy group etc. Among these groups, a methoxy or ethoxy group is preferable. The aryl group represented by each of $R_2$ and $R_3$ can include a phenyl group etc. The aralkyl group represented by each of $R_2$ and $R_3$ can include a benzyl group etc. The group represented by each of $R_2$ and $R_3$ in the formula (I) is more preferably hydrogen.

The C1 to C6 alkyl group, the aryl group and the aralkyl group represented by $R_4$ in the formula (I) can include the same groups as described above.

The C1 to C3 hydroxyalkyl group represented by each of $R_5$ and $R_7$ can include a hydroxymethyl group, hydroxyethyl group and hydroxypropyl group. Among these groups, a hydroxymethyl or hydroxyethyl group is preferable.

The acyl group represented by each of $R_6$ and $R_8$ is preferably an acyl group derived from an aliphatic carboxylic acid. The acyl group includes an acetyl group and a propionyl group, among which an acetyl group is preferable. The C1 to C3 alkyl group represented by each of $R_6$ and $R_8$ can include the same groups as described above.

Z in the formula (I) above is a sulfur atom, an oxygen atom, a selenium atom or $CR_9R_{10}$, among which a sulfur atom is preferable.

The C1 to C3 alkyl group represented by each of $R_9$ and $R_{10}$ can include the same groups as described above.

The anion represented by $X^-$ in the formula (I) above includes, for example, a halogen ion, a boron halide ion, a phosphorus compound ion, a halogeno oxyacid ion, a fluorosulfate ion, a methyl sulfate ion, and a tetraphenyl boron compound ion having a halogen atom or a haloalkyl group as a substituent on a phenyl ring. The halogen ion includes a fluorine ion, chlorine ion, bromine ion and iodine ion. The boron halide ion includes $BF_4^-$, $BCl_4^-$ and $BBr_4^-$. Among these ions, a bromine ion or $BF_4^-$ is preferable.

Examples of the dye of the formula (I) are shown below:

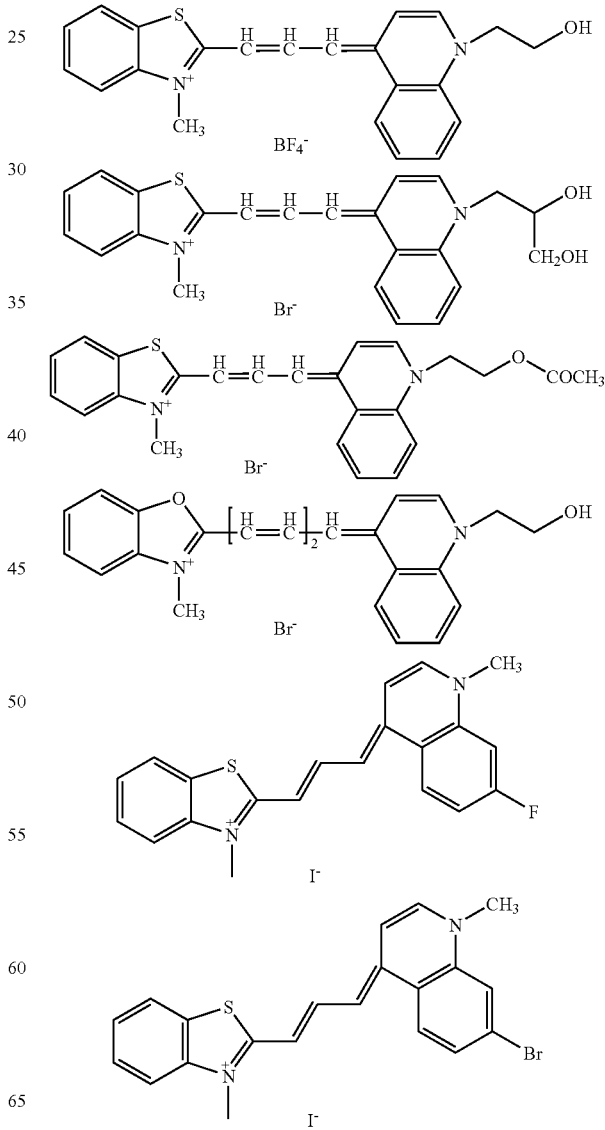

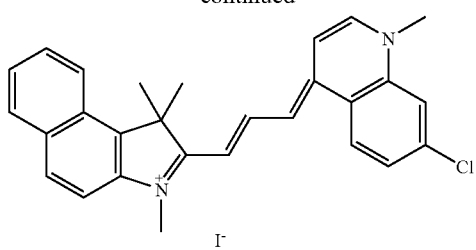
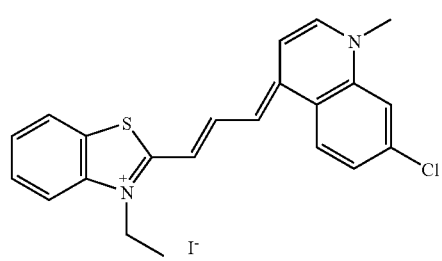
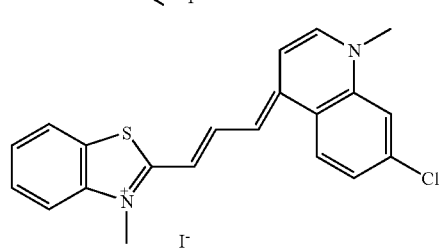
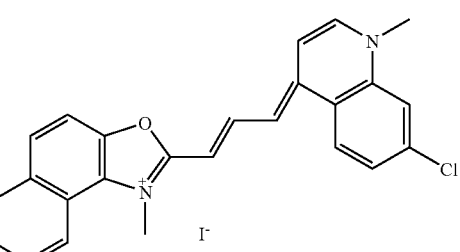
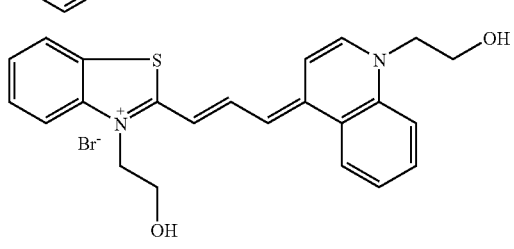
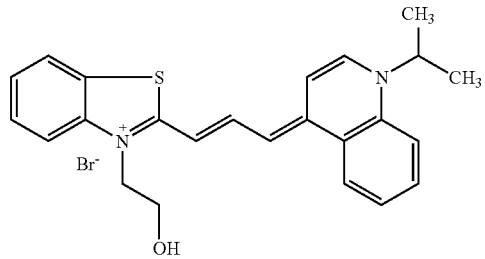
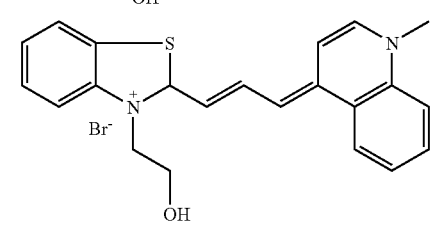
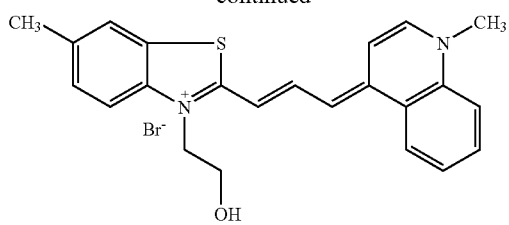
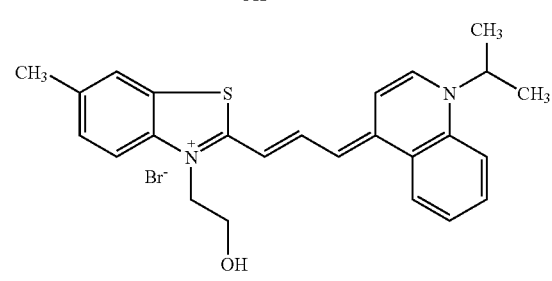
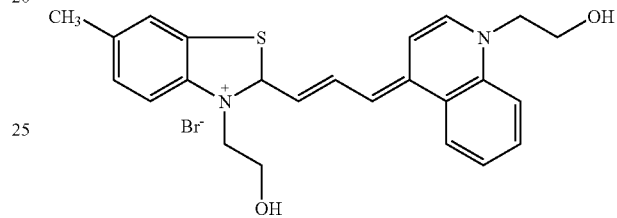
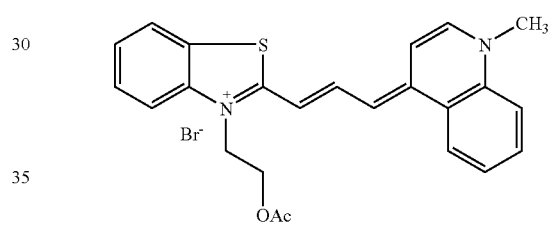
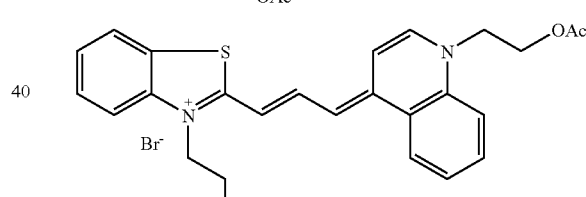
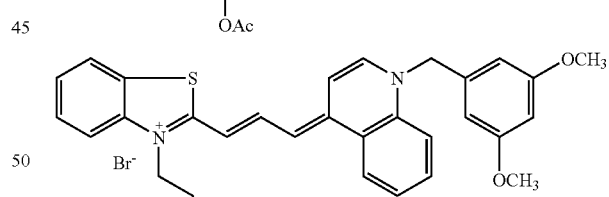
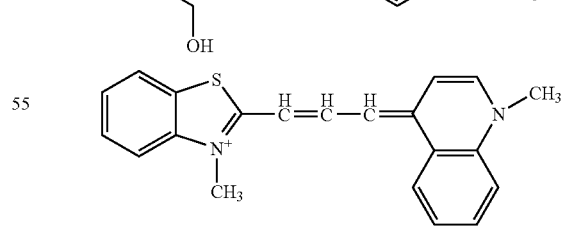
Thiazole blue
Among the dyes represented by the formula (I), the dyes wherein n=1 can be synthesized for example by the following method. First, N,N-di-substituted formamidine is reacted with a compound represented by the following formula (V):

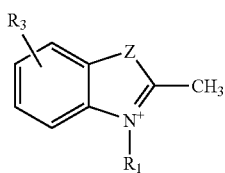

(V)

The product obtained by the reaction is reacted with a quinoline derivative represented by formula (VI) below and then treated with sodium borofluoride.

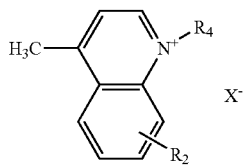

(VI)

The dyes of the formula (I) wherein n=1 can thereby be synthesized.

The dyes of the formula (I) wherein n=2 can be synthesized by the same reaction as for the dyes wherein n=1 except that for example, malondialdehyde bis(phenylimine) salt is used in place of N,N-di-substituted formamidine.

Besides the nucleic acid-staining cyanine dyes described above, dyes such as New Methylene Blue and Oxazine 750 are also known as dyes for reticulocyte and may be used as the second dye.

The dye for staining platelet is contained in the reagent such that the concentration of the dye, though varying depending on the type of dye or the type of reagent, becomes 0.01 to 10 ppm when mixed with a sample.

For example, when the dye for staining platelet is contained in the PLT reagent, the dye is contained in the PLT reagent such that the concentration of the dye, though varying depending on the type of dye, becomes preferably 0.01 to 5 ppm, more preferably 0.05 to 2.0 ppm or so, when mixed with a sample. Particularly when Capri blue GON is used as the dye for staining platelet to discriminate platelets from lipid particles, the dye is contained in the PLT reagent such that the concentration of the dye, when mixed with a sample, becomes preferably 0.1 to 5.0 ppm, more preferably 0.2 to 2.0 ppm. When Capri blue GON is used to discriminate platelets from fragmented red blood cells, the dye is contained in the PLT reagent such that the concentration of the dye, when mixed with a sample, becomes preferably 0.1 to 2.0 ppm, more preferably 0.2 to 1.0 ppm. When Nile blue is used to discriminate platelets from lipid particles, the dye is contained in the PLT reagent such that the concentration of the dye, when mixed with a sample, becomes preferably 0.05 to 5.0 ppm, more preferably 0.1 to 2.0 ppm. When Nile blue is used to discriminate platelets from fragmented red blood cells, the dye is contained in the PLT reagent such that the concentration of the dye, when mixed with a sample, becomes preferably 0.05 to 2.0 ppm, more preferably 0.1 to 1.0 ppm. When brilliant cresyl blue ALD is used to discriminate platelets from lipid particles, the dye is contained in the PLT reagent such that the concentration of the dye, when mixed with a sample, becomes preferably 0.1 to 5.0 ppm, more preferably 0.5 to 2.0 ppm. When brilliant cresyl blue ALD is used to discriminate platelets from fragmented red blood cells, the dye is contained in the PLT reagent such that the concentration of the dye, when mixed with a sample, becomes preferably 0.2 to 5.0 ppm, more preferably 0.5 to 2.0 ppm.

For further improvement in discrimination of platelets from other blood cells and contaminants, it is preferable that the concentration of the dye in the PLT reagent is in the range defined above.

When the dye for staining platelet is contained as the first dye in the RET/PLT reagent, the dye is contained in the reagent such that the concentration of the first dye, though varying depending on the type of dye, becomes preferably 0.01 to 10 ppm, more preferably 0.1 to 2.0 ppm or so, when mixed with a sample. Particularly when Capri blue GON is used as the first dye to discriminate platelets from lipid particles and fragmented red blood cells, the first dye is contained in the RET/PLT reagent such that the concentration of the first dye, when mixed with a sample, becomes preferably 0.2 to 3.0 ppm, more preferably 0.5 to 2.0 ppm. When Nile blue is used to discriminate platelets from lipid particles and fragmented red blood cells, the first dye is contained in the RET/PLT reagent such that the concentration of the first dye, when mixed with a sample, becomes preferably 0.1 to 2.0 ppm. When brilliant blue ALD is used to discriminate platelets from lipid particles and fragmented red blood cells, the first dye is contained in the RET/PLT reagent such that the concentration of the first dye, when mixed with a sample, becomes preferably 0.5 to 3.0 ppm, more preferably 1.0 to 2.0 ppm.

For further improvement in discrimination of platelets from other blood cells and contaminants, it is preferable that the concentration of the first dye in the RET/PLT reagent is in the range defined above.

The second dye is contained in the RET/PLT reagent such that the concentration of the second dye, though varying depending on the type of dye, becomes preferably 0.1 to 50 ppm, more preferably 0.5 to 10 ppm or so, when mixed with a sample. When the concentration of the second dye in the RET/PLT reagent is in the range defined above, reticulocytes can be distinguished from other blood cells and contaminants.

The second dye for staining reticulocyte in the composition of the RET/PLT reagent can rapidly penetrate into reticulocyte and stain RNA in the cell.

Preferably the RET/PLT reagent further comprises a multivalent anion for suppressing nonspecific staining of red blood cell. The multivalent anion includes a sulfate ion, phosphate ion, carbonate ion and multivalent carboxylate ion. Compounds capable of supplying these ions include citric acid, sulfuric acid, phosphoric acid, EDTA and alkali metal salts thereof. The RET/PLT reagent can include one or more of these compounds as multivalent anions.

The proportion of the multivalent anions may be at least 50% of the whole anion component in the reagent. The proportion of the multivalent anions is preferably at least 70% of the whole anion component in the reagent.

By incorporating the multivalent anions, nonspecific staining of red blood cell can be prevented, and discrimination among reticulocyte, platelet and red blood cell can be facilitated.

The PLC reagent and RET/PLT reagent can contain a buffer for keeping pH constant. The buffer may be contained at a concentration of several mM to about 100 mM. The buffer is not particularly limited insofar as it is usually used, and for example, a carboxylate, a phosphate, Good's buffer, taurine and triethanolamine can be used depending on desired pH.

The pH of the PLT reagent and RET/PLT reagent is preferably in the range of 6.0 to 11.0, more preferably 7.0 to 10.0, still more preferably 8.0 to 9.5. When the pH is too lower than the above range, red blood cells are made fragile and easily destructed, so the amount of fragmented red blood cells as contaminants may be increased. When the pH is too higher than the above range, acidic functional groups on a membrane of red blood cell are dissociated so that the red blood cell may easily bind to the cationic dye, thus increasing nonspecific staining of fragmented red blood cell.

When a compound capable of supplying the multivalent ions has buffering action in the RET/PLT reagent, the compound can also be used as a buffer.

The osmotic pressure of the PLT reagent and RET/PLT reagent is preferably 150 to 600 mOsm/kg, more preferably 200 to 300 mOsm/kg. An osmotic pressure in this range is near to physiological osmotic pressure, and can thus prevent hypotonic hemolysis of red blood cells.

To maintain the osmotic pressure described above, the PLT and RET/PLT reagent can contain an osmotic pressure-compensating agent. The osmotic pressure-compensating agent may be a conventionally used agent, and examples include alkali metal salts such as propionates and sugars such as glucose and mannose. Alkali metal halides such as NaCl and alkaline earth metal halides can also be used. These osmotic pressure-compensating agents can be used alone or as a mixture of two or more thereof. When the above buffer can be used to regulate the osmotic pressure of the reagent in the above range, the osmotic pressure-compensating agent may not be used.

The PLT reagent and RET/PLT reagent can contain a staining promoter for promoting penetration of the dye into a cell. The staining promoter includes surfactants and is particularly preferably a cationic surfactant. A preferable cationic surfactant is represented by the following formula (VII):

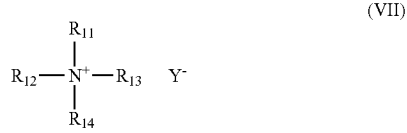

(VII)

wherein $R_{11}$ represents a C8 to C12 alkyl group, $R_{12}$, $R_{13}$ and $R_{14}$ independently represent a C1 to C6 alkyl group, and $Y^-$ represents an anion.

The C8 to C12 alkyl group represented by $R_{11}$ in the formula (VII) may be either linear or branched. The C8 to C12 alkyl group represented by $R_{11}$ includes, for example, an octyl group, decyl group, lauryl group, cetyl group and myristyl group.

The C1 to C6 alkyl group represented by each of $R_{12}$, $R_{13}$ and $R_{14}$ in the formula (VII) may be either linear or branched. The C1 to C6 alkyl group represented by each of $R_{12}$, $R_{13}$ and $R_{14}$ includes, for example, a methyl group, ethyl group, propyl group, butyl group, isobutyl group, sec-butyl group, tert-butyl group, pentyl group and hexyl group. Among these groups, a methyl or ethyl group is preferable.

The anion represented by $Y^-$ in the formula (VII) is preferably a bromine ion or a chlorine ion.

Preferable examples of the cationic surfactant represented by the formula (VII) include decyltrimethylammonium bromide (DTAB), octyltrimethylammonium bromide (OTAB), lauryltrimethylammonium chloride (LTAC), cetyltrimethylammonium chloride (CTAC) and myristyltrimethylammonium bromide (MTAB). These cationic surfactants may be used alone or as a mixture of two or more thereof.

The above cationic surfactant is contained in the PLT reagent or RET/PLT reagent preferably at such a concentration that when the PLT reagent or RET/PLT reagent is mixed with a sample, the cationic surfactant can promote staining of platelet, or reticulocyte and platelet, and does not cause destruction of red blood cells. Such concentration varies depending on the type of the cationic surfactant, but is usually about 50 to 20000 ppm. For example, when DTAB is used, its concentration in the reagent is preferably about 500 to 3000 ppm. When LTAC for example is used, its concentration in the reagent is preferably about 100 to 500 ppm.

The PLT reagent and RET/PLT reagent may contain, for example, preservatives such as 2-pyridylthio-1-oxide sodium and β-phenethyl alcohol, in addition to the components described above.

The PLT reagent can be produced by dissolving the dye for staining platelet, and arbitrary components (a buffer, an osmotic pressure-compensating agent, a staining promoter, a preservative etc.), in a suitable solvent at the suitable concentrations described above. The solvent is not particularly limited insofar as it can stably dissolve these components. Examples of the solvent include water and water-soluble organic solvents. As the water-soluble organic solvent, it is possible to use ethanol, dimethyl sulfoxide, ethylene glycol or a mixed solvent thereof.

The respective components may be dissolved in an arbitrary order without limitation to the order of dissolving them in solvent. Alternatively, the components are previously dissolved in different suitable solvents respectively, and just before use, the respective solutions may be mixed for use as the PLT reagent. Such form also falls under the scope of the invention. For example, if the dye for staining platelet is unstable in an aqueous solution, the dye may be dissolved in a water-soluble organic solvent and mixed just before use with an aqueous solution containing the other components to constitute a solution for use as the PLT reagent.

The RET/PLT reagent can be produced by dissolving the first dye for staining platelet, the second dye for staining reticulocyte, and arbitrary components (multivalent anions, a buffer, an osmotic pressure-compensating agent, a staining promoter, a preservative etc.), in a suitable solvent at the suitable concentrations described above. The solvent is not particularly limited insofar as it can stably dissolve these components. Examples of the solvent include water and water-soluble organic solvents. As the water-soluble organic solvent, it is possible to use ethanol, dimethyl sulfoxide, ethylene glycol or a mixed solvent thereof.

The respective components may be dissolved in an arbitrary order without limitation to the order of dissolving them in solvent. Alternatively, the components are previously dissolved in different suitable solvents respectively, and just before use, the respective solutions may be mixed for use as the RET/PLT reagent. Such form also falls under the scope of the invention. For example if the first and second dyes is unstable in an aqueous solution, the dyes may be dissolved in a water-soluble organic solvent and mixed just before use with an aqueous solution containing the other components to constitute a solution for use as the RET/PLT reagent. The first and second dyes can be dissolved in the same water-soluble organic solvent or in different water-soluble organic solvents.

The PLT reagent thus produced can be mixed and reacted with a sample to prepare a measurement sample thereby staining platelets which may be contained in the sample, or the RET/PLT reagent thus produced can be mixed and reacted with a sample to prepare a measurement sample thereby staining reticulocytes and platelets which may be contained in the sample. In this specification, the sample refers to blood (whole blood, platelet-rich plasma (PRP) etc.) or a bone marrow aspirate collected from the biological body (particularly mammals including humans), or to a sample obtained by diluting the blood or blood marrow aspirate with a suitable solution such as a buffer solution.

The mixing ratio (volume ratio) of the PLT reagent (or the RET/PLT reagent) to a sample is preferably established such that reagent:sample=100:1 to 1000:1. The temperature at which the PLC reagent (or the RET/PLT reagent) is reacted with a sample is preferably about 25 to 50° C., more preferably about 35 to 45° C. The reaction time, though varying depending on the type of dye, is preferably about 10 seconds to 5 minutes, more preferably about 20 seconds to 2 minutes, still more preferably 20 seconds to 60 seconds.

The measurement sample prepared as described above is irradiated with light, and scattered light and fluorescence emitted from cells in the measurement sample are measured. An apparatus for light irradiation is preferably a flow cytometer. When a flow cytometer is used, the measurement sample is introduced into a flow cell of the flow cytometer, cells in the measurement sample flowing in the flow cell are irradiated with light.

A light source of the flow cytometer used is not particularly limited, and a light source with suitable wavelengths (for example in the vicinity of 600 to 680 nm) for exciting the dye for staining platelet or the first dye for staining platelet and the second dye for staining reticulocyte can be used. The light source includes, for example, a red semiconductor laser and a He—Ne laser. Particularly, a semiconductor laser is preferable because it is inexpensive as compared with a gas laser.

The scattered light emitted from cells upon irradiation with light in the flow cytometer may be either forward-scattered light (in the vicinity of a light receiving angle of 0 to 20°) or side-scattered light (in the vicinity of a light receiving angle of 90°). The forward-scattered light may be either forward low-angle scattered light (in the vicinity of a light receiving angle of 1 to 5°) or forward high-angle scattered light (in the vicinity of a light receiving angle of 6 to 20°). The scattered light is known to be a parameter reflecting information on cell size.

For fluorescence emitted from cells upon irradiation with light in the flow cytometer, a suitable wavelength of received light can be selected depending on the dye used.

Based on the scattered light and fluorescence obtained as described above by using the PLT reagent, scattergrams can be prepared to detect platelets by distinguishing platelets from other blood cells and contaminants such as lipid particles. The platelets thus detected can also be counted. Suitable analysis software is preferably used in detecting and counting platelets.

Based on the scattered light and fluorescence obtained as described above by using the RET/PLT reagent, scattergrams can be prepared to detect reticulocytes and platelets by distinguishing reticulocytes and platelets from other blood cells and contaminants such as lipid particles. The reticulocytes and platelets thus detected can also be counted. Suitable analysis software is preferably used in detecting and counting reticulocytes and platelets.

In another aspect of the invention, there is provided a reagent kit for analyzing platelet (hereinafter referred to sometimes as PLT reagent kit) comprising a first reagent containing a buffer for keeping pH constant during measurement and a second reagent containing a dye for staining platelet, wherein the dye is at least one member selected from the group consisting of Capri blue, Nile blue and brilliant cresyl blue.

The buffer in the first reagent in the PLT reagent kit may the same as described above.

The first and second reagents in the PLT reagent kit may be prepared by dissolving the buffer and the platelet-staining dye in a suitable solvent, respectively.

The PLT reagent kit may further contain an osmotic pressure-compensating agent, a staining promoter, a preservative etc. which can be contained arbitrarily in the PLT reagent. These components may be contained in the first or second reagent in the PLT reagent kit or may be contained in other reagents in the kit.

By mixing the reagents in the PLT reagent kit with a sample, a measurement sample can be prepared. The order of mixing the respective reagents in the PLT reagent with a sample is not particularly limited. The mixing ratio (volume ratio) is established preferably such that the total of the respective reagents in the reagent kit:sample=100:1 to 1000:1.

The method for preparing a measurement sample by using the PLT reagent kit, the method for measuring scattered light and fluorescence from the measurement sample and the method for detecting platelets on the basis of the scattered light and fluorescence can be the same as in the PLT reagent described above.

In still another aspect of the invention, there is provided a reagent kit for analyzing reticulocyte and platelet (hereinafter referred to sometimes as RET/PLT reagent kit), comprising a first reagent containing a first dye for staining platelet, which is selected from the group consisting of Capri blue, Nile blue and brilliant cresyl blue, and a second reagent containing a second dye for staining reticulocyte. The RET/PLT reagent kit can further comprise a third reagent containing a buffer for keeping pH constant during measurement.

The buffer can be the same as described above.

The first reagent, the second reagent and the third reagent in the RET/PLT reagent kit may be prepared by dissolving the first dye, the second dye and the buffer in suitable solvents, respectively.

In a further other aspect of the invention, there is provided a RET/PLT reagent kit, comprising a first reagent containing a buffer for keeping pH constant during measurement and a second reagent containing a first dye for staining platelet, which is selected from the group consisting of Capri blue, Nile blue and brilliant cresyl blue, and a second dye for staining reticulocyte.

The buffer can be the same as described above.

The first reagent and the second reagent in the RET/PLT reagent kit may be prepared by dissolving the buffer and the first and second dyes in suitable solvents, respectively.

The RET/PLT reagent kit may further comprise multivalent anions, an osmotic pressure-compensating agent, a staining promoter, a preservative etc. which can be contained arbitrarily in the RET/PLT reagent. These reagents may be contained in the first, second or third reagent or may be contained in other reagents in the kit.

By mixing the respective reagents in the RET/PLT reagent kit with a sample, a measurement sample can be prepared. The order of mixing the respective reagents in the PET/PLT reagent with a sample is not particularly limited. The mixing ratio (volume ratio) is established preferably such that the total of the respective reagents in the reagent kit:sample=100:1 to 1000:1.

The method for preparing a measurement sample by using the RET/PLT reagent kit, the method for measuring scattered light and fluorescence from the measurement sample and the method for detecting reticulocytes and platelets on the basis of the scattered light and fluorescence can be the same as in the RET/PLT reagent described above.

The present invention also relates to a method for analyzing platelet, comprising the steps of:

preparing a measurement sample by mixing a sample and a dye for staining platelet, which is selected from the group consisting of Capri blue, Nile blue and brilliant cresyl blue;

measuring scattered light and fluorescence emitted from cells in the measurement sample by irradiating the cells with light; and detecting platelet on the basis of the measured scattered light and fluorescence. Specifically, the PLT reagent as described above can be mixed with a sample to prepare a measurement sample. Then, the resulting measurement sample is analyzed with a known blood analyzer equipped with a light source (for example, a flow cytometer), whereby scattering light intensity and fluorescence intensity can be obtained form the measurement sample. Using suitable analysis software, platelets can, on the basis of the scattering light intensity and fluorescence intensity, be discriminated from other blood cells and contaminants such as lipid particles, thereby classifying the platelets. Further, the classified platelets may be counted with suitable analysis software. The scattering light intensity includes forward-scattering light intensity and side-scattering light intensity.

Further, the present invention relates to a method for analyzing reticulocyte and platelet, comprising the steps of:

preparing a measurement sample by mixing a sample, a first dye for staining platelet, which is selected from the group consisting of Capri blue, Nile blue and brilliant cresyl blue, and a second dye for measuring reticulocyte;

measuring scattered light and fluorescence emitted from cells in the measurement sample by irradiating the cells with light; and detecting reticulocyte and platelet on the basis of the measured scattered light and fluorescence. Specifically, the RET/PLT reagent as described above can be mixed with a sample to prepare a measurement sample. Then, the resulting measurement sample is analyzed with a known blood analyzer equipped with a light source (for example, a flow cytometer), whereby scattering light intensity and fluorescence intensity can be obtained form the measurement sample. Using suitable analysis software, reticulocytes and platelets can, on the basis of the scattering light intensity and fluorescence intensity, be discriminated from other blood cells and contaminants such as lipid particles, thereby classifying the reticulocytes and platelets respectively. Further, the classified reticulocytes and platelets may be counted with suitable analysis software. The scattering light intensity includes forward-scattering light intensity and side-scattering light intensity.

EXAMPLES

Hereinafter, the present invention is described in more detail by reference to the Examples, but these examples are not intended to limit the scope of the invention.

Examples 1 to 3 and Comparative Examples 1 to 12

(Reagent)

A reagent for analyzing platelet having the following composition was produced.

(1) Dye Solution

| Dye for staining platelet | Concentration shown below |
|---|---|
| Ethylene glycol | 1 L |

(2) Diluent

| Tricine (buffer) | 1.8 g |
|---|---|
| Trisodium citrate dihydrate (multivalent anion) | 29 g |
| Lauryltrimethylammonium chloride (LTAC) | 0.15 g |
| Purified water (adjusted to pH 9.0 and an osmotic pressure of 200 mOsm/kg · $H_2O$) | 1 L |

As the dye for staining platelet, each of the dyes shown below was used at the concentration shown below. The final concentration of the dye upon mixing the reagent with a sample is shown in parentheses. Chemical formulae of these dyes are shown in FIG. 1.

Examples:

| | | |
|---|---|---|
| 1. | Capri blue GON (Croma) | 20.5 ppm (0.4 ppm) |
| 2. | Nile blue chloride (Tokyo Chemical Industry Co., Ltd.) | 20.5 ppm (0.4 ppm) |
| 3. | Brilliant cresyl blue ALD (Sigma) | 51.25 ppm (1 ppm) |

Comparative Examples:

| | | |
|---|---|---|
| 1. | Azure A (Sigma) | 102.5 ppm (2 ppm) |
| 2. | Azure D (Sigma) | 102.5 ppm (2 ppm) |
| 3. | Azure C (Sigma) | 102.5 ppm (2 ppm) |
| 4. | Methylene blue NNX (Sigma) | 102.5 ppm (2 ppm) |
| 5. | Cresyl violet acetate (Sigma) | 1025 ppm (20 ppm) |
| 6. | Basic Green 5 (Tokyo Chemical Industry Co., Ltd.) | 1025 ppm (20 ppm) |
| 7. | Methylene blue (Sigma) | 102.5 ppm (2 ppm) |
| 8. | New Methylene Blue (Croma) | 1025 ppm (20 ppm) |
| 9. | Toluidine blue (Tokyo Chemical Industry Co., Ltd.) | 102.5 ppm (2 ppm) |
| 10. | Oxazine 750 (Nacalai Tesque, Inc) | 102.5 ppm (2 ppm) |
| 11. | Oxazine 1 (Exciton) | 1025 ppm (20 ppm) |
| 12. | Oxazine 4 (Exciton) | 1025 ppm (20 ppm) |

(Method)

1 mL of the diluent was pipetted into a tube and warmed in a water bath at 40° C.

20 μL of the dye solution and 5 μL whole blood as a sample from a healthy human were added to the diluent and then incubated at 40° C. for 25 seconds to prepare a measurement sample. Thereafter, the measurement sample was introduced into a detecting part having a 633-nm excitation light source in a flow cytometer. In the detecting part, cells in the measurement sample were irradiated with exciting light, and a scattering light signal and fluorescence signal emitted from the cells were detected. The obtained signals were analyzed to measure platelets in the measurement sample.

(Results)

Scattergrams obtained by measurement using the respective dye solutions described above are shown in FIGS. 1A, 1B and 1C. Scattergram (1) shows forward scattering light intensity on the ordinate and fluorescence intensity on the abscissa. In scattergram (2) is the same as scattergram (1) except that the ordinate has been converted into log. In scattergram (2), the region where platelets appear is shown in solid line.

As can be seen from the result in FIGS. 1A to C, Capri blue, Nile blue or brilliant cresyl blue can distinguish platelets more clearly with higher fluorescence intensity from other blood cells than by the other dyes. When a sample is contaminated with contaminants such as lipid particles, a cluster of contaminations appears in a position of low fluorescence intensity on the scattergram. Accordingly, it can be seen that when Capri blue, Nile blue or brilliant cresyl blue is used as the dye for staining platelet, platelets can be distinguished from contaminants.

Example 4

Examination of a Suitable Concentration of Capri Blue in the Reagent for Analyzing Platelet In this example, platelet was measured in the same manner as in Example 1 except that Capri blue GON was contained as the platelet-staining dye in the dye solution in in Example 1, and also that Capri blue GON was contained in the dye solution such that the final concentration of Capri blue GON became 0.1 to 5.0 ppm when the reagent was mixed with a sample. As the sample, whole blood from a healthy subject, blood containing fragmented red blood cells, and lipid-containing blood were respectively used.
(Results)

The resultant scattergrams are shown in FIG. 2. Scattergram (1) shows forward scattering light intensity on the ordinate and fluorescence intensity on the abscissa. Scattergram (2) is the same as scattergram (1) except that the ordinate has been converted into log. Scattergram (3) is an enlargement of an area including and around the region where platelets appear in scattergram (2). In scattergram (3), the region where platelets appear is shown in solid line. From this result, it was found that when the concentration of Capri blue GON is 0.1 to 5.0 ppm, platelet can be clearly distinguished from contaminants even if lipid occurs as contaminant. It was also found that when the concentration of Capri blue GON is 0.1 to 2.0 ppm, platelet can be clearly distinguished from contaminants even if fragmented red blood cell occurs as contaminant.

Example 5

Examination of a Suitable Concentration of Nile Blue in the Reagent for Analyzing Platelet In this example, platelet was measured in the same manner as in Example 2 except that Nile blue chloride was contained as the dye for staining platelet in the dye solution in Example 2, and also that Nile blue chloride was contained in the dye solution such that the final concentration of Nile blue chloride became 0.05 to 5 ppm when the reagent was mixed with a sample. As the sample, whole blood from a healthy subject, blood containing an increased amount of fragmented red blood cells, and lipid-containing blood were respectively used.
(Results)

Figure 3A:
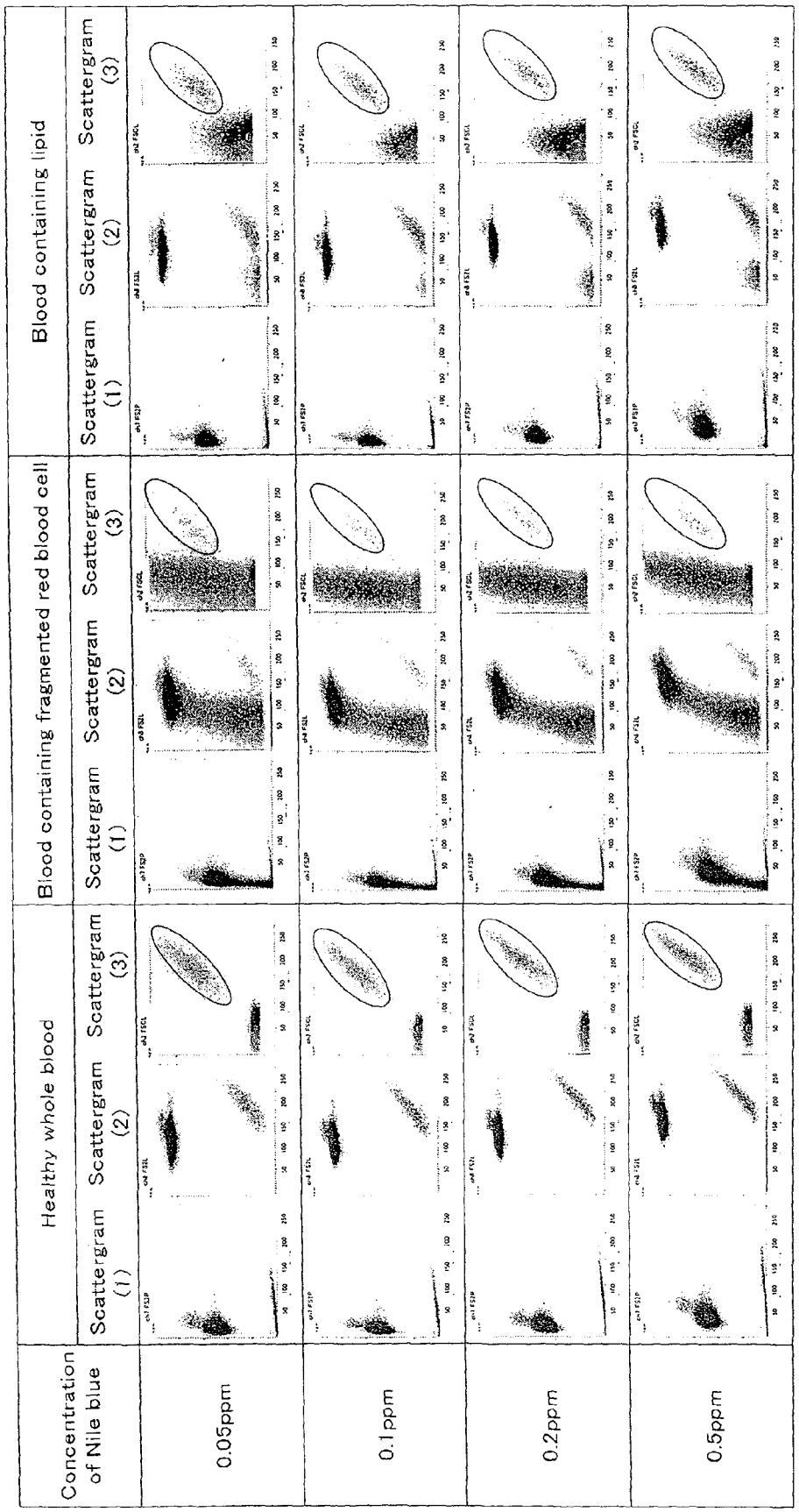
FIGS. 3A and B show scattergrams obtained by measurement using each platelet measurement reagent with different concentrations of Nile blue.
Figure 3B:
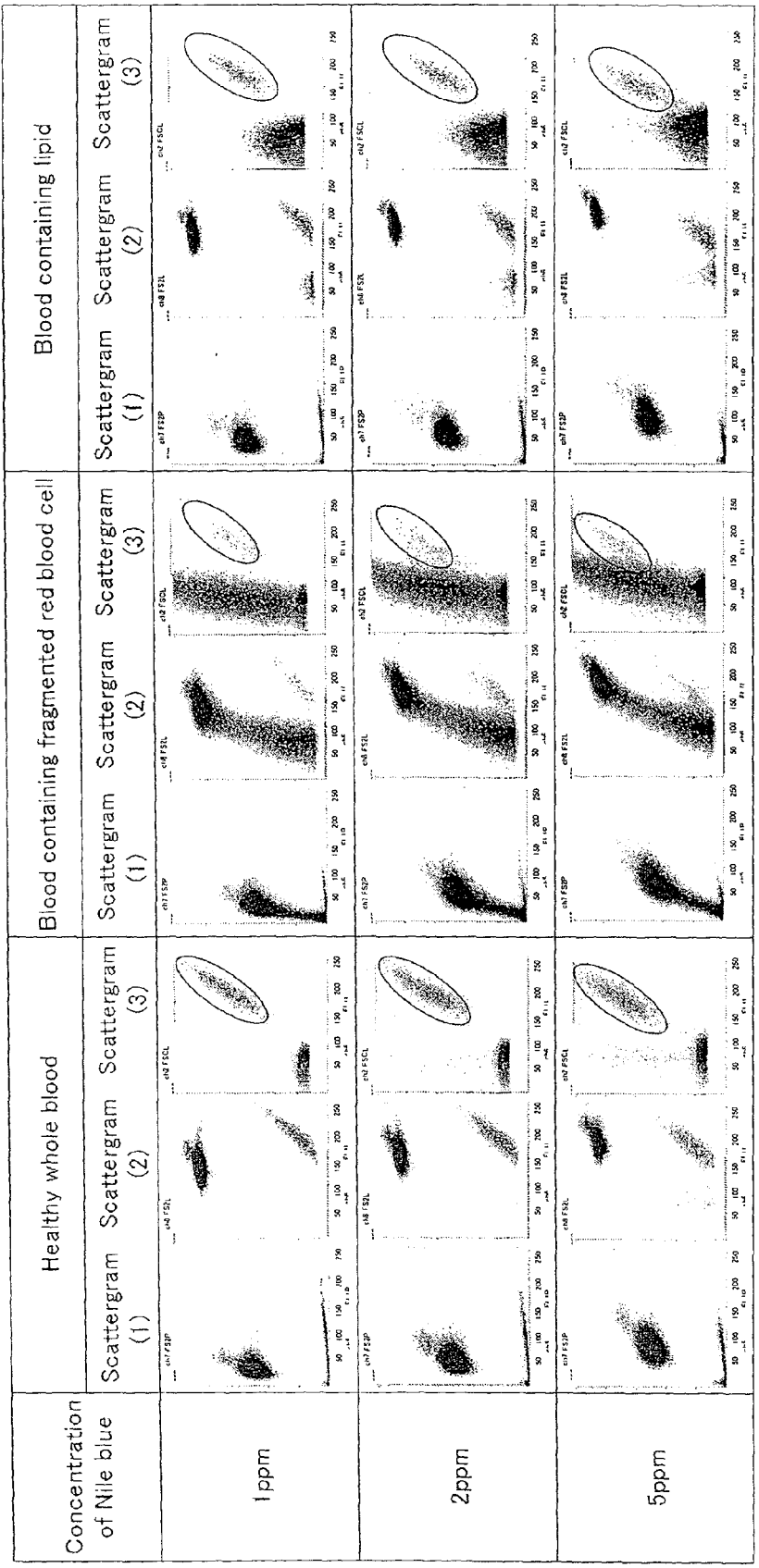

The resultant scattergrams are shown in FIGS. 3A and 3B. Scattergram (1) shows forward scattering light intensity on the ordinate and fluorescence intensity on the abscissa. Scattergram (2) is the same as scattergram 1 except that the ordinate has been converted into log. Scattergram (3) is an enlargement of an area including and around the region where platelets appear in scattergram (2). In scattergram (3), the region where platelets appear is shown in solid line. From this result, it was found that when the concentration of Nile blue chloride is 0.05 to 5.0 ppm, platelet can be clearly distinguished from contaminants even if lipid occurs as contaminant. It was also found that when the concentration of Nile blue chloride is 0.05 to 2.0 ppm, platelet can be clearly distinguished from contaminants even if fragmented red blood cell occurs as contaminant.

Example 6

Examination of a Suitable Concentration of Brilliant Cresyl Blue in the Reagent for Analyzing Platelet In this example, platelet was measured in the same manner as in Example 3 except that brilliant cresyl blue ALD was contained as the dye for staining platelet in the dye solution in Example 3, and also that brilliant cresyl blue ALD was contained in the dye solution such that the final concentration of brilliant cresyl blue ALD became 0.1 to 10 ppm when the reagent was mixed with a sample. As the sample, whole blood from a healthy subject, blood containing fragmented red blood cells, and lipid-containing blood were respectively used.
(Results)

Figure 4A:
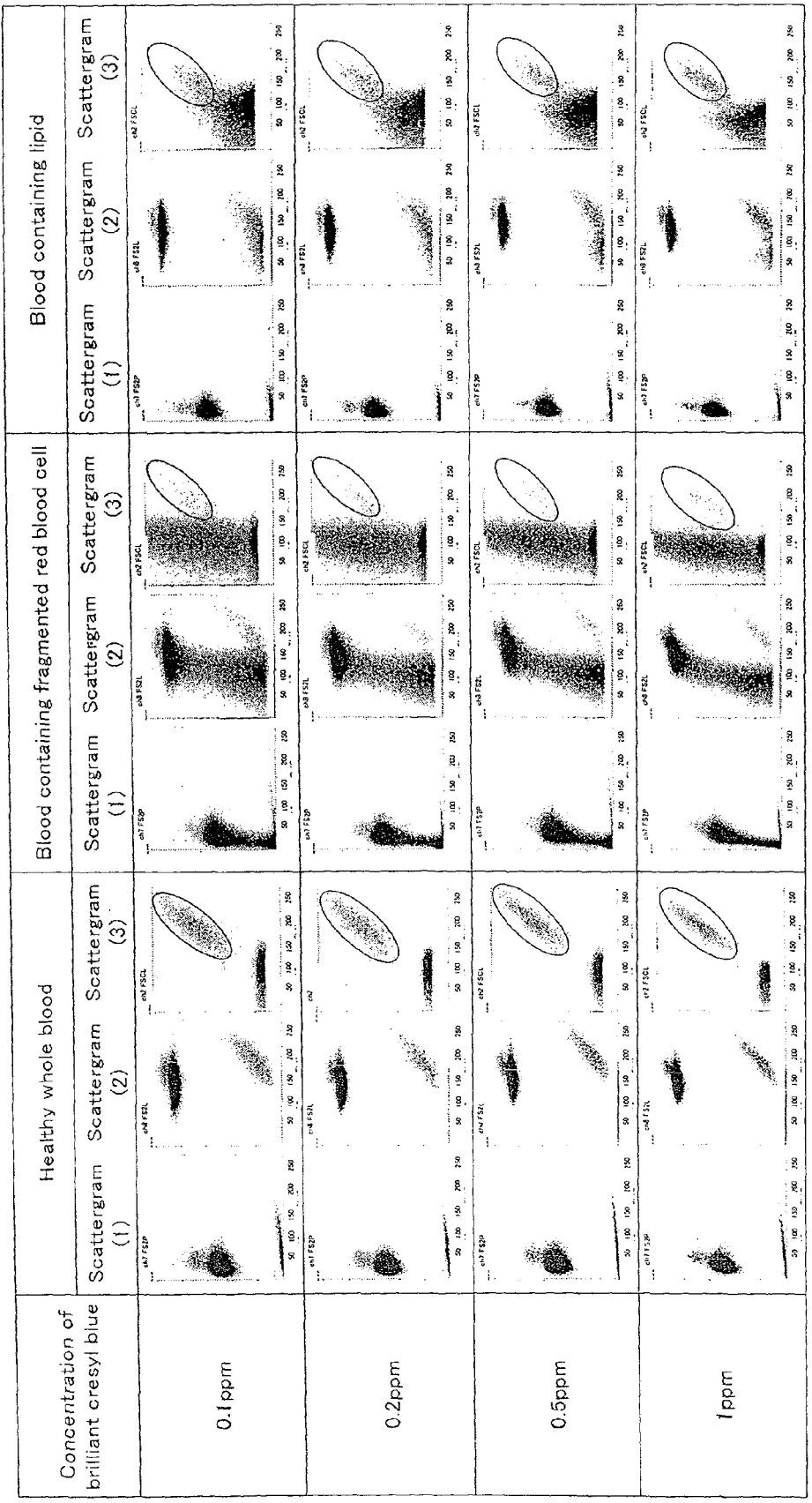
FIGS. 4A and B show scattergrams obtained by measurement using each reagent for analyzing platelet with different concentrations of brilliant cresyl blue.
Figure 4B:
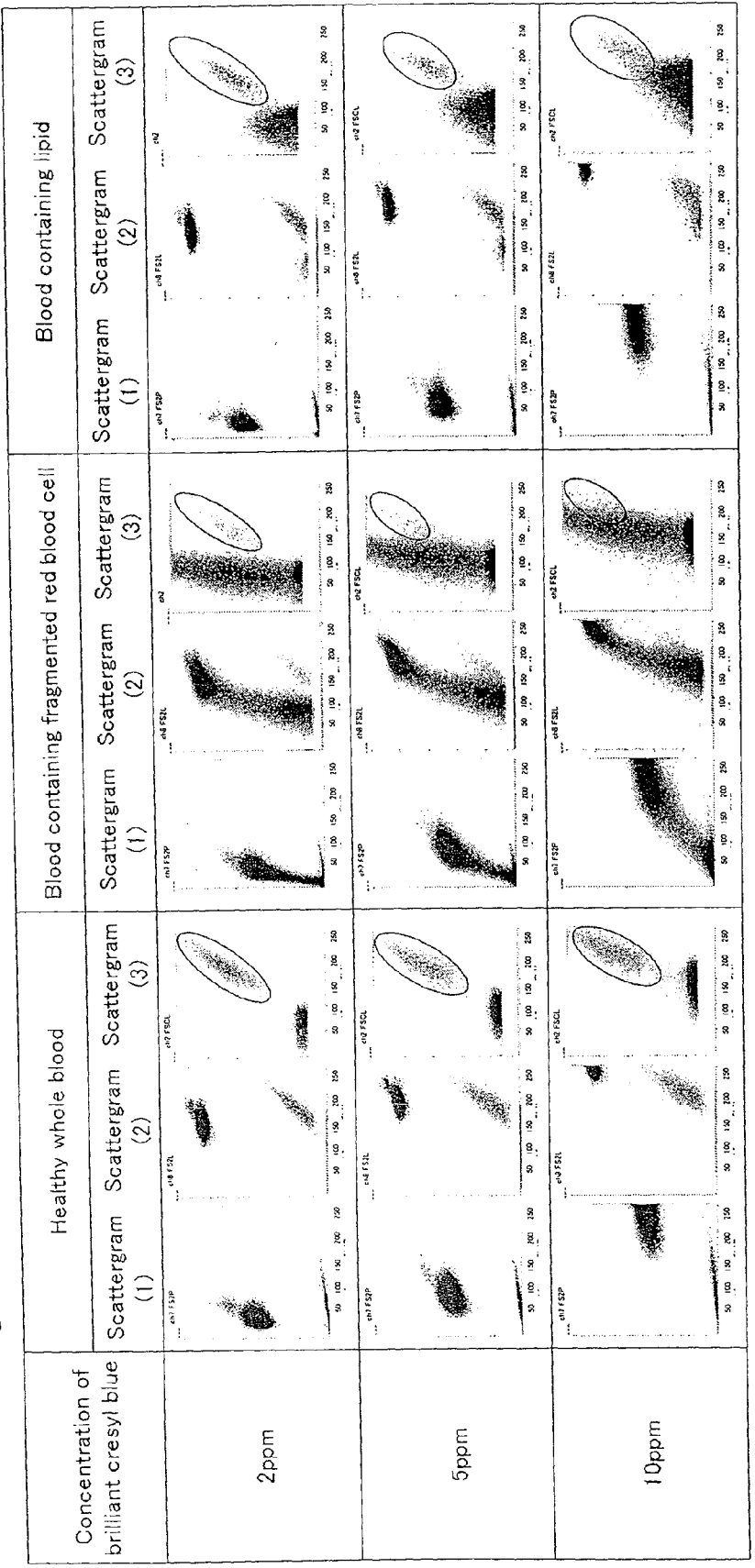

The resultant scattergrams are shown in FIGS. 4A and 4B. Scattergram (1) shows forward scattering light intensity on the ordinate and fluorescence intensity on the abscissa. Scattergram (2) is the same as scattergram (1) except that the ordinate has been converted into log. Scattergram (3) is an enlargement of an area including and around the region where platelets appear in scattergram (2). In scattergram (3), the region where platelets appear is shown in solid line. From this result, it was found that when the concentration of brilliant cresyl blue ALD is 0.1 to 10.0 ppm, platelet can be clearly distinguished from contaminants even if lipid occurs as contaminant. It was also found that when the concentration of brilliant cresyl blue ALD is 0.2 to 2.0 ppm, platelet can be clearly distinguished from contaminants even if fragmented red blood cell occurs as contaminant.

Example 7

Comparison Between the Measurement Method of the Invention and a Conventional Method (Immunostaining Method)

Correlation between the measurement method of the invention and a conventional method using immunostaining was examined in this example.
(Measurement of Platelet by Immunostaining)

The number of platelets was measured according to a standard method recommended by International Committee for Standardization of Hematology (ICSH), as a conventional method described in American Journal of Clinical Pathologists (2001):115, pp. 460-464. This method is based on immunostaining with an antibody specific for a surface antigen of platelet. That is, 5 µL of fluorescein isothiocyanate (FITC)-labeled anti-human CD41a antibody (manufactured by Becton Dickinson), 5 µL of FITC-labeled anti-human CD61 antibody (manufactured by Becton Dickinson) and 100 µL of phosphate-buffered saline (PBS, pH 7.2 to 7.4, manufactured by Wako Pure Chemical Industries, Ltd.) were pipetted into a tube. 5 µL of a sample (blood) was added thereto and stirred gently. The resulting mixture was incubated at room temperature for 15 minutes in the dark. 4.85 mL of PBS was added to the mixture. The resulting mixture was measured with FACS Canto (manufactured by Becton Dickinson) to give platelet measurement result "a" and red blood cell measurement result "b". The sample (blood) used herein was measured with an automatic blood cell counter XE-2100 (manufactured by Sysmex Corporation) to determine number of red blood cells "c", and finally, the following equation was utilized to calculate the number of platelets by the conventional method. Number of platelets=Number of red blood cells "c"×(platelet measurement result "a"/red blood cell measurement result "b")

(Measurement Method of the Invention)

Capri blue GON was contained as the dye for staining platelet in the dye solution in Example 1. Capri blue GON was contained in the dye solution such that when the reagent was mixed with a sample, the final concentration of Capri blue GON became 1.2 ppm. Nile blue chloride was contained as the dye for staining platelet in the dye solution in Example 2. Nile blue chloride was contained in the dye solution such that when the reagent was mixed with a sample, the final concentration of Nile blue chloride became 0.5 ppm. In the same manner as in Examples 1 and 2 except for the above, platelets were detected and the number of platelets was calculated. As the sample, the same blood as used in immunostaining was used.

(Results)

Figure 5A:
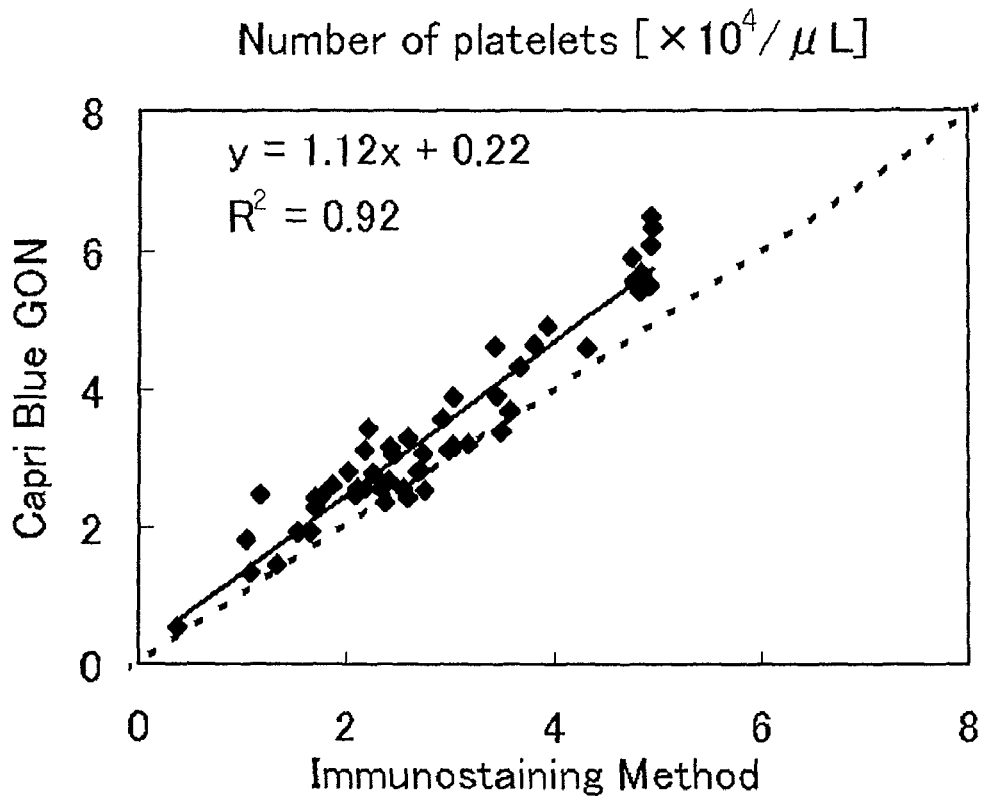
FIGS. 5A and B show graphs showing the correlation between the number of platelets as determined by the method in one embodiment of the invention and the number of platelets as determined by a conventional method.
Figure 5B:
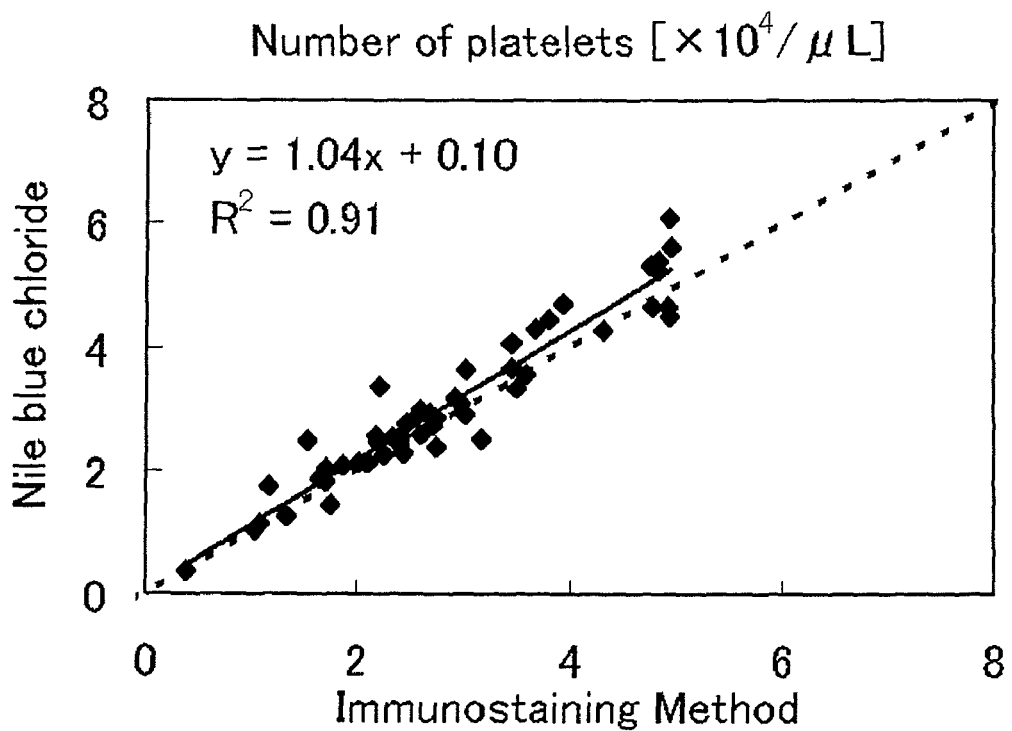

Graphs wherein the number of platelets as determined by the measurement method of the invention is plotted against the number of platelets as determined by the immunostaining method are shown in FIGS. 5A and 5B. FIG. 5A shows the result of the method of the invention using Capri blue GON. FIG. 5B shows the result of the method of the invention using Nile blue chloride.

As can be seen from FIGS. 5A and 5B, the results obtained by the method of the invention, as compared with the results obtained by the conventional method using immunostaining, show excellent correlation with less scattering.

Example 8

In this example, the reagent for analyzing reticulocyte and platelet, comprising a first dye for staining platelet and a second dye for staining reticulocyte, was prepared to measure reticulocyte and platelet.

(Reagent)

The composition of the reagent is as follows:

(1) Dye Solution

| First dye | Concentration shown below |
|---|---|
| Second dye | Concentration shown below |

(2) Diluent

| Tricine (buffer) | 1.8 g |
|---|---|
| Trisodium citrate dihydrate (multivalent anion) | 29 g |
| Lauryltrimethylammonium chloride (LTAC) | 0.15 g |
| Purified water | 1 L |

As the second dye for staining reticulocyte, a dye shown in the following formula was used. The second dye was contained in the dye solution such that when the reagent was mixed with a sample, the final concentration of the second dye became 0.5 ppm, 6 ppm or 10 ppm.

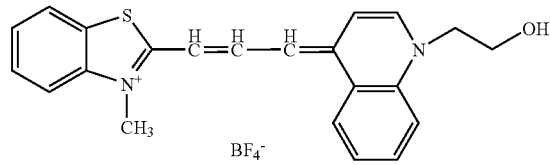

As the first dye for staining platelet, Capri blue GON, Nile blue chloride or brilliant cresyl ALD was used. The first dye was contained in the dye solution such that when the reagent was mixed with a sample, the final concentration of the dye became 1 ppm for Capri blue GON, 0.5 ppm for Nile blue chloride, or 1.5 ppm for brilliant cresyl blue ALD.

As the sample, whole blood from a healthy human, blood containing fragmented red blood cells, and lipid-containing blood were used respectively. Measurement was carried out in the same manner as in Example 1.

(Results)

Figure 6A:
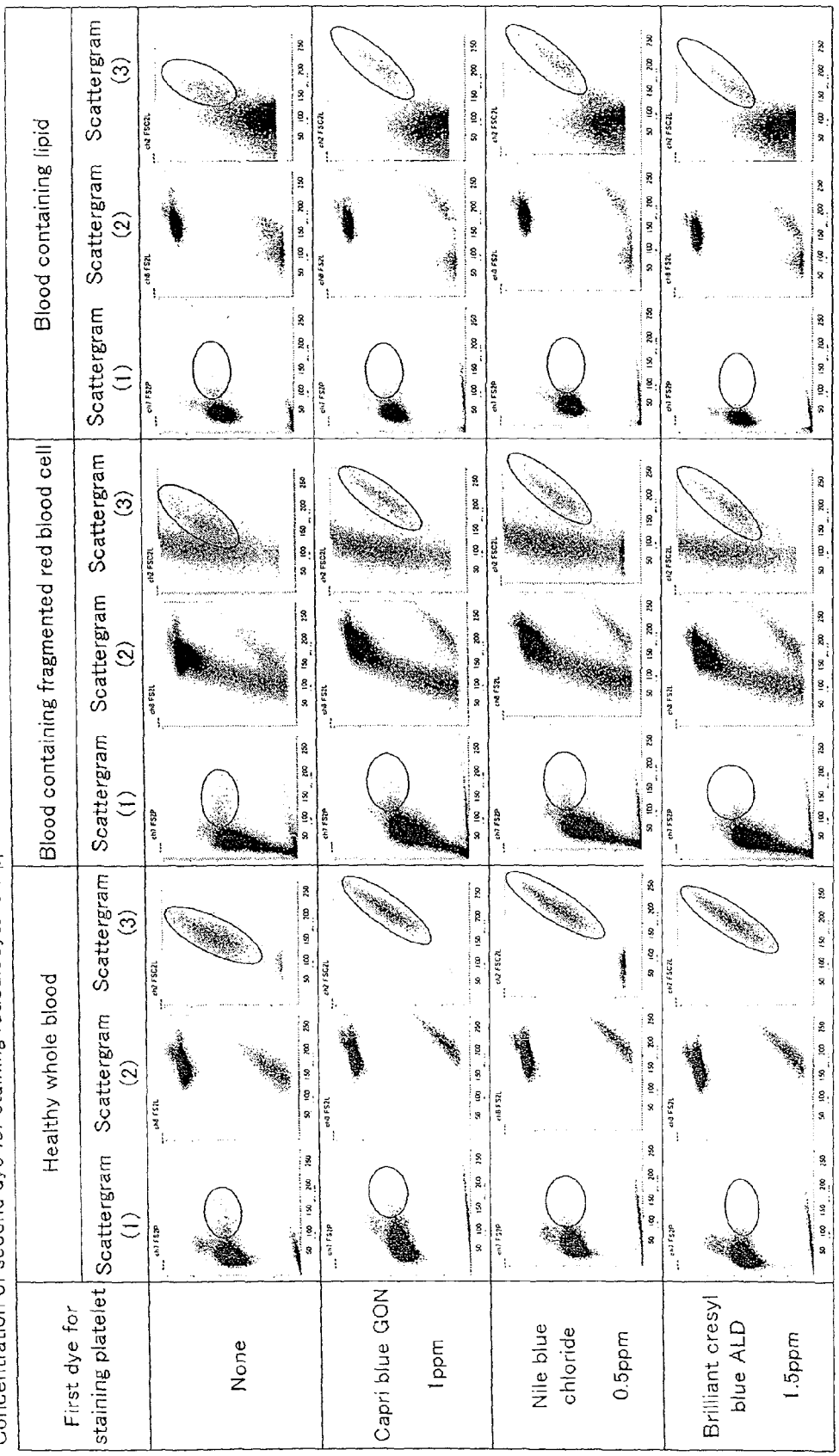
FIGS. 6A to C show scattergrams obtained by measurement using each reagent for analyzing reticulocyte and platelet with different concentrations of a dye for staining reticulocyte.
Figure 6B:
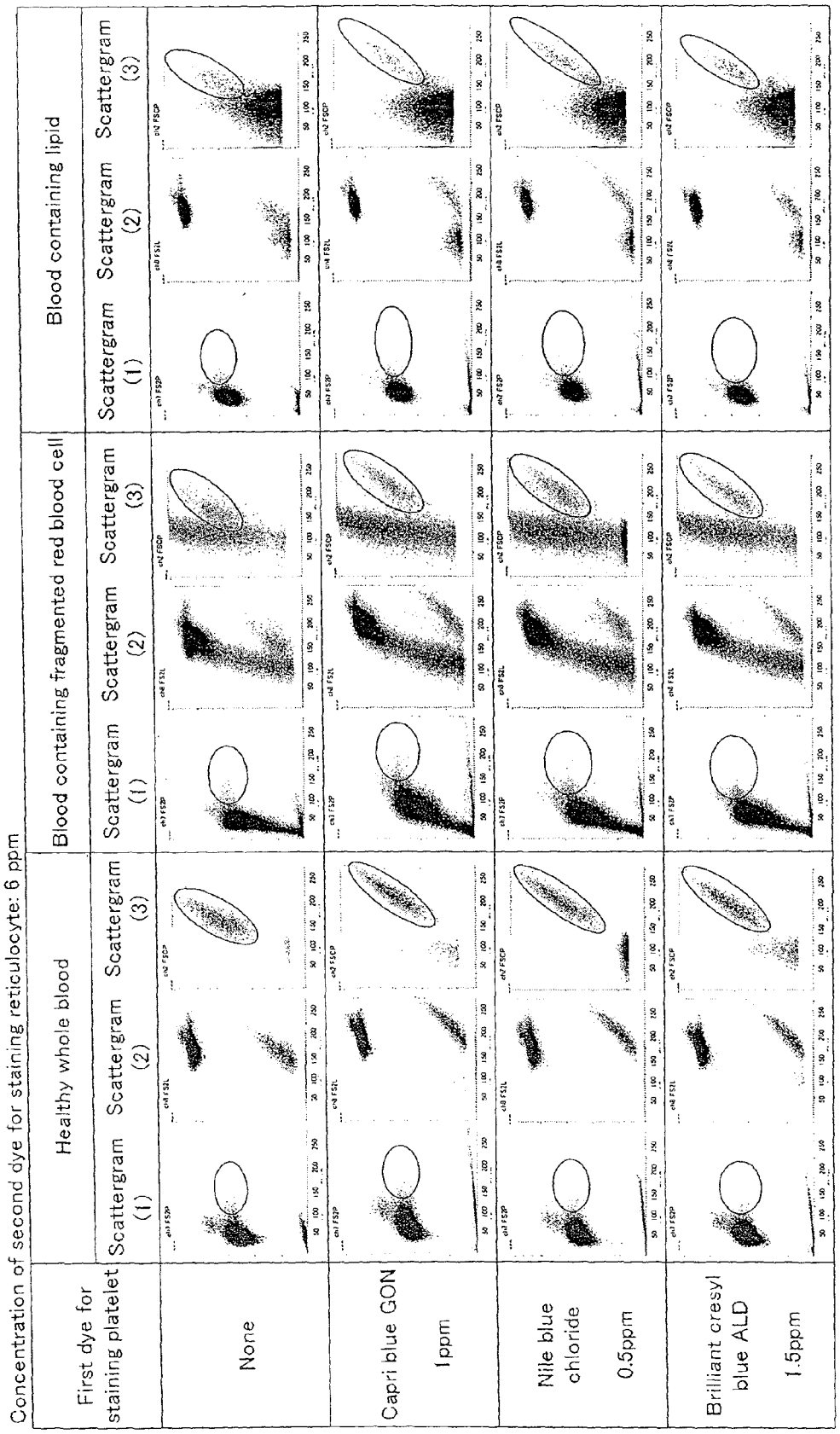
Figure 6C:
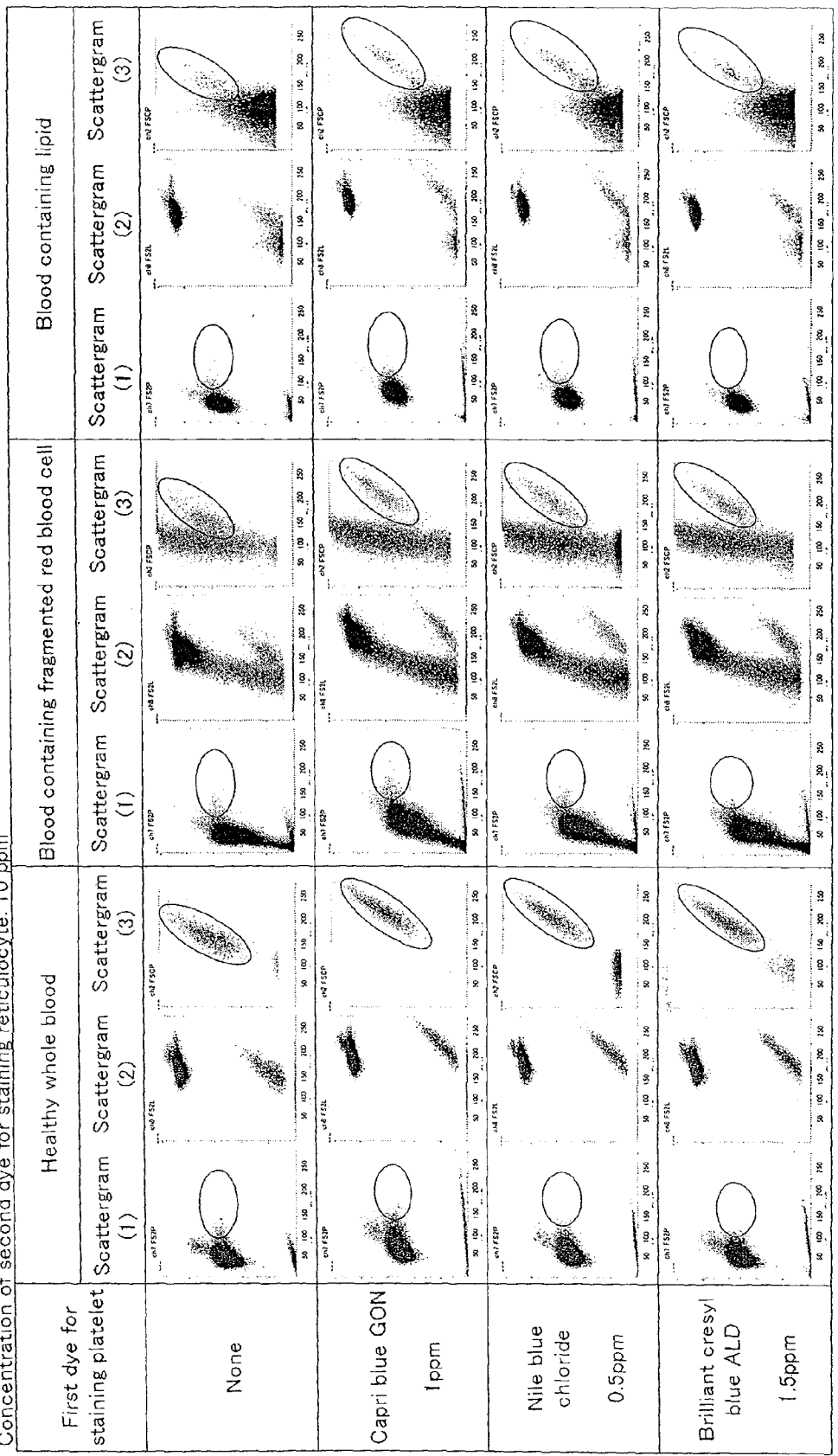

The resultant scattergrams are shown in FIGS. 6A, 6B and 6C. Scattergram (1) shows forward scattering light intensity on the ordinate and fluorescence intensity on the abscissa. Scattergram (2) is the same as scattergram (1) except that the ordinate has been converted into log. Scattergram (3) is an enlargement of an area including and around the region where platelets appear in scattergram (2). In scattergram (1), the region where reticulocytes appear is shown in solid line. In scattergram (3), the region where platelets appear is shown in solid line.

For comparison, scattergrams wherein the first dye for staining platelet was not added to the dye solution are also shown in FIGS. 6A, 6B and 6C.

From the results in FIGS. 6A to 6C, it can be seen that when the concentration of the second dye is in the range of 0.5 to 10 ppm, platelets and reticulocytes can be distinguished more clearly even in the presence of fragmented red blood cells and lipid by the reagent to which the first dye was added than by the reagent to which the first dye was not added.

Example 9

In this example, the second dye for staining reticulocyte used in Example 8 was contained in the dye solution in Example 8. The second dye was contained in the dye solution such that the final concentration of the second dye became 0.5 ppm, 6 ppm or 10 ppm when the reagent was mixed with a sample. Capri blue GON was contained as the first dye for staining platelet in this dye solution. Capri blue GON was contained in the dye solution such that the final concentration of Capri blue GON became 0.5 ppm, 1 ppm or 2 ppm when the reagent was mixed with a sample. The sample used was the same as in Example 8. Measurement was carried out in the same manner as in Example 8.

(Results)

Figure 7A:
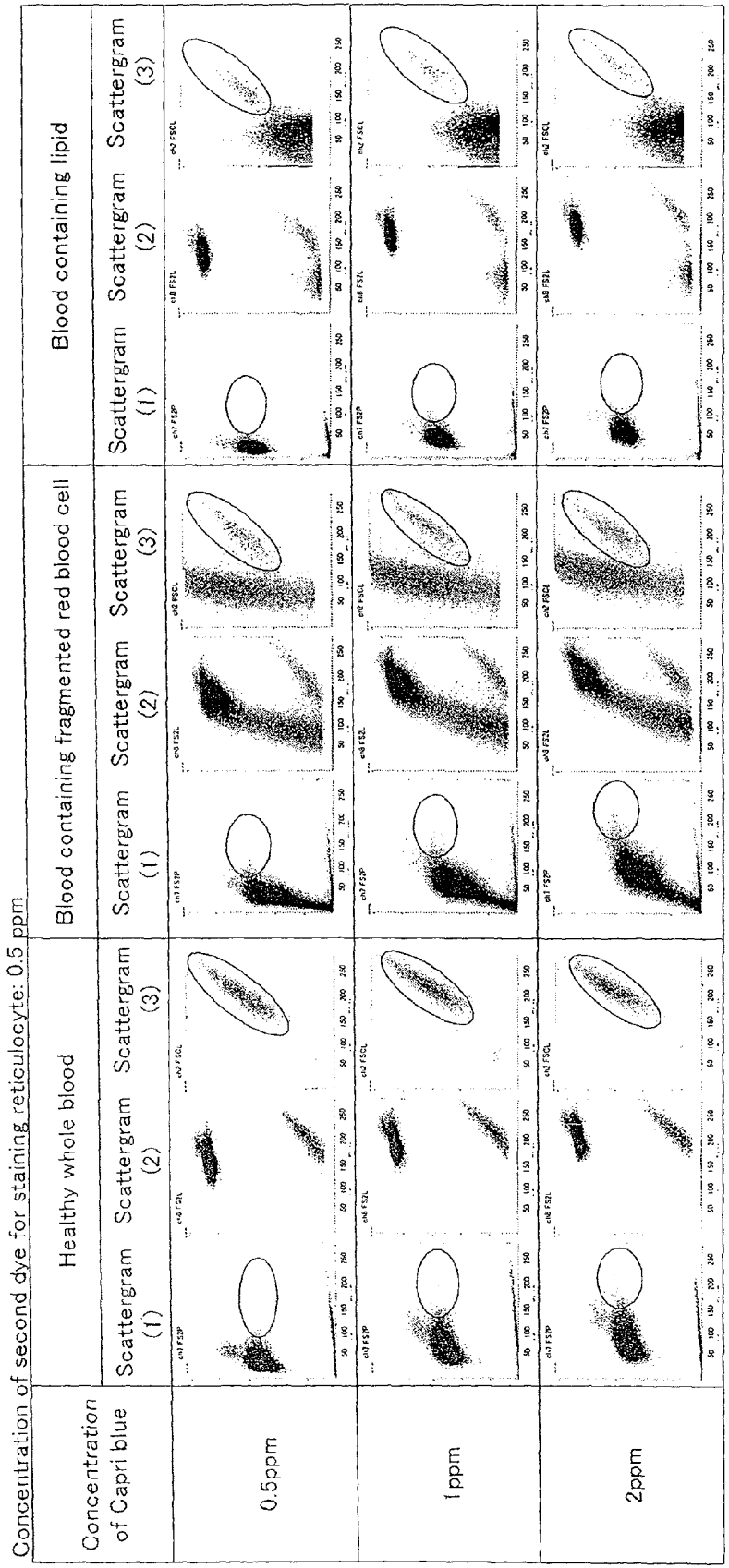
FIGS. 7A to C show scattergrams obtained by measurement using each reagent for analyzing reticulocyte and platelet with different concentrations of a dye for staining reticulocyte and different concentrations of a dye (Capri blue) for staining platelet.
Figure 7B:
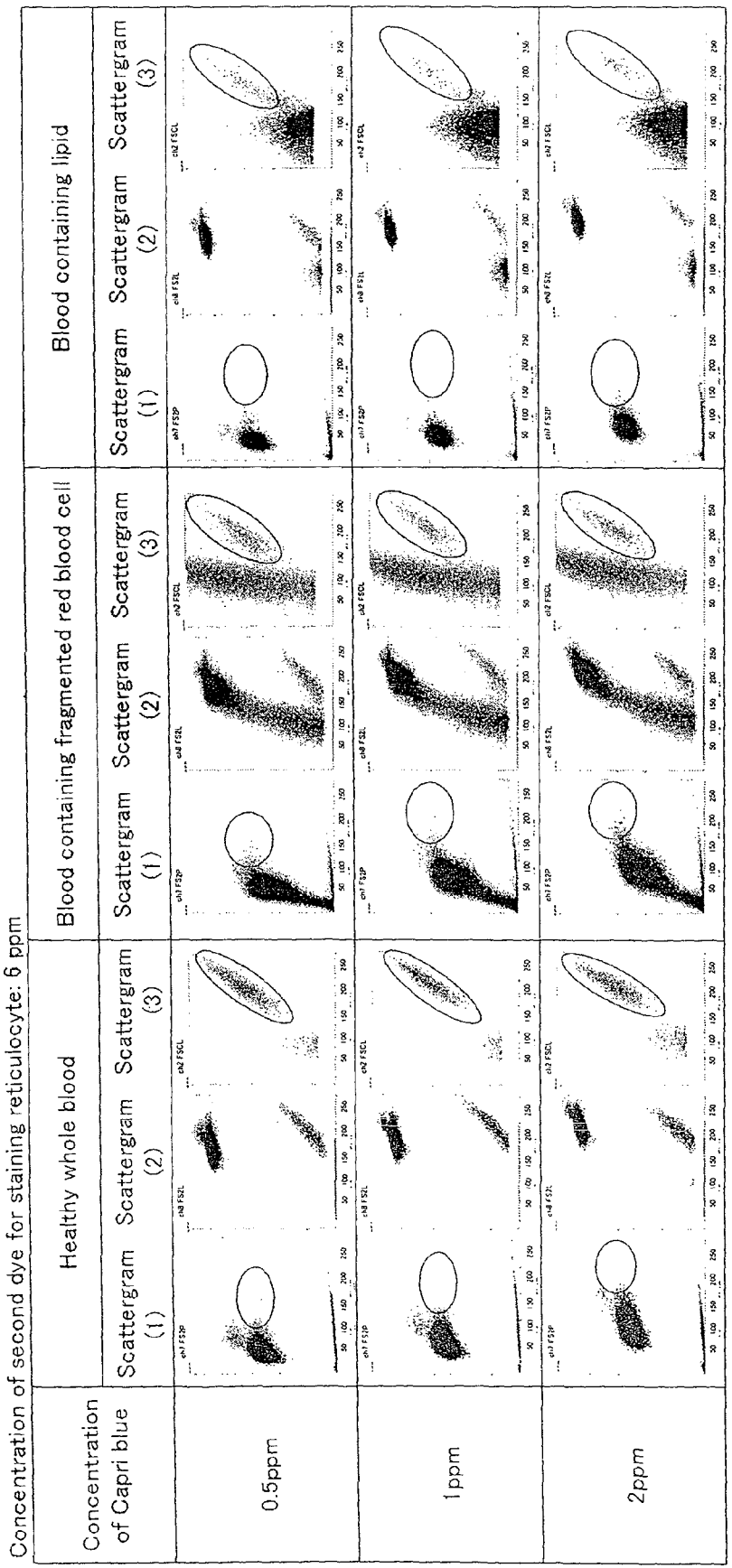
Figure 7C:
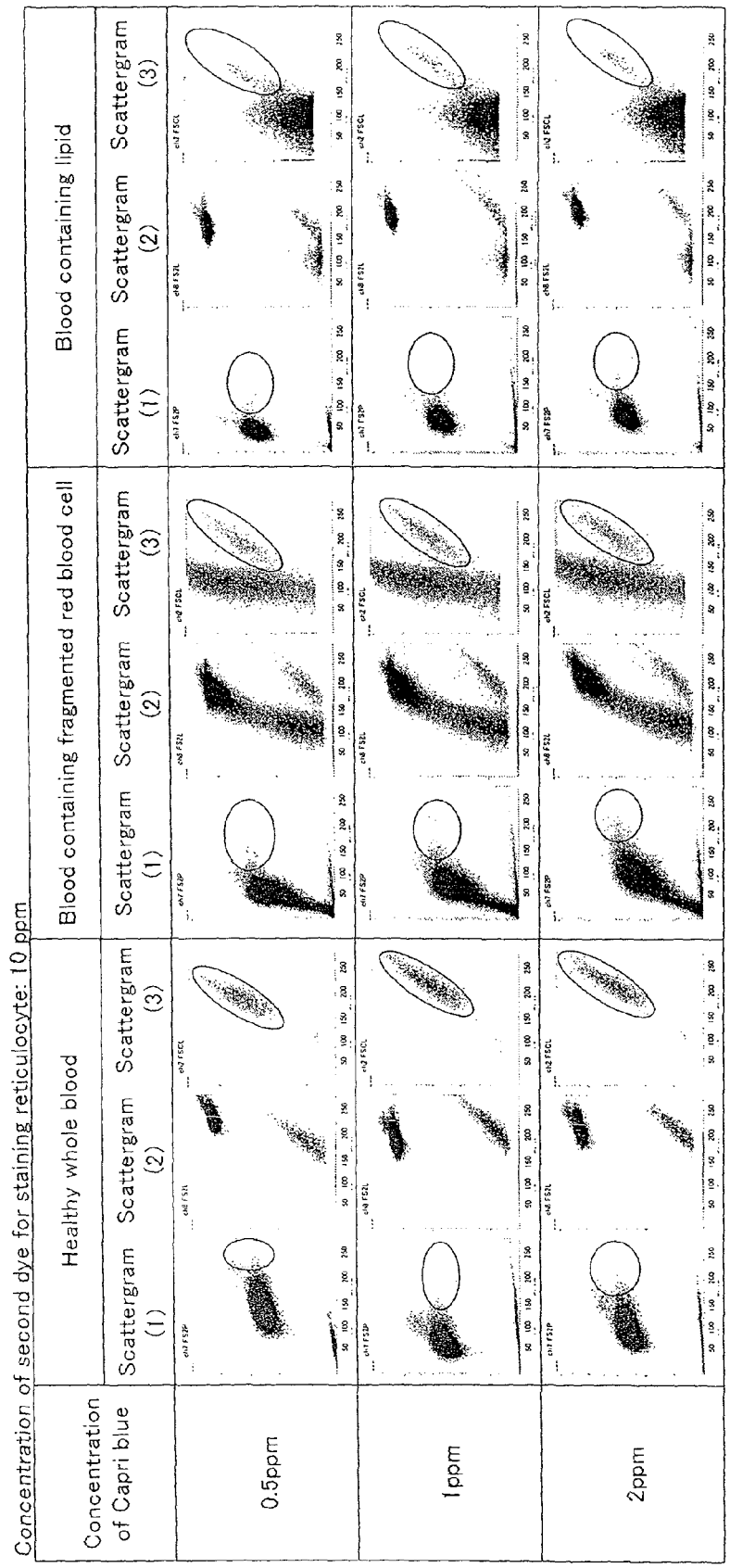

The resultant scattergrams are shown in FIGS. 7A, 7B and 7C. Scattergram (1) shows forward scattering light intensity on the ordinate and fluorescence intensity on the abscissa. Scattergram (2) is the same as scattergram (1) except that the ordinate has been converted into log. Scattergram (3) is an enlargement of an area including and around the region where platelets appear in scattergram (2). In scattergram (1), the region where reticulocytes appear is shown in solid line. In scattergram (3), the region where platelets appear is shown in solid line. From this result, it was found that when the concentration of the second dye is 0.5 ppm to 10 ppm and Capri blue GON is 0.5 to 2.0 ppm, reticulocytes and platelets can be clearly distinguished from contaminants even if lipid and fragmented red blood cells occur as contaminants.

Example 10

In this example, the second dye for staining reticulocyte used in Example 8 was contained in the dye solution in Example 8. The second dye was contained in the dye solution such that the final concentration of the second dye became 0.5 ppm, 6 ppm or 10 ppm when the reagent was mixed with a sample. Nile blue chloride was also contained as the first dye for staining platelet in this dye solution. Nile blue chloride was contained in the dye solution such that the final concentration of Nile blue chloride became 0.1 ppm, 0.5 ppm or 2 ppm when the reagent was mixed with a sample. The sample used was the same as in Example 8. Measurement was carried out in the same manner as in Example 8.

(Results)

Figure 8A:
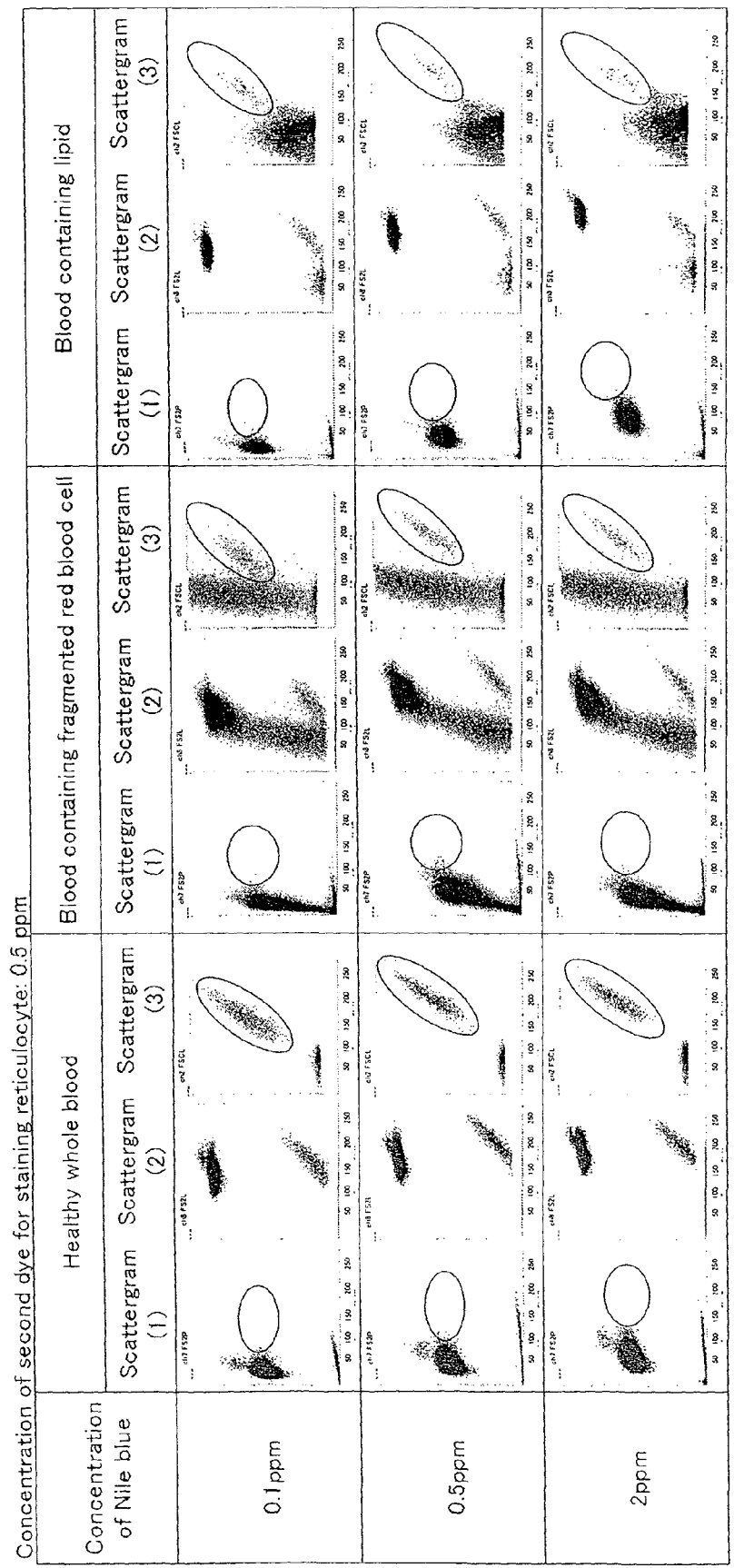
FIGS. 8A to C show scattergrams obtained by measurement using each reagent for analyzing reticulocyte and platelet with different concentrations of a dye for staining reticulocyte and different concentrations of a dye (Nile blue) for staining platelet.
Figure 8B:
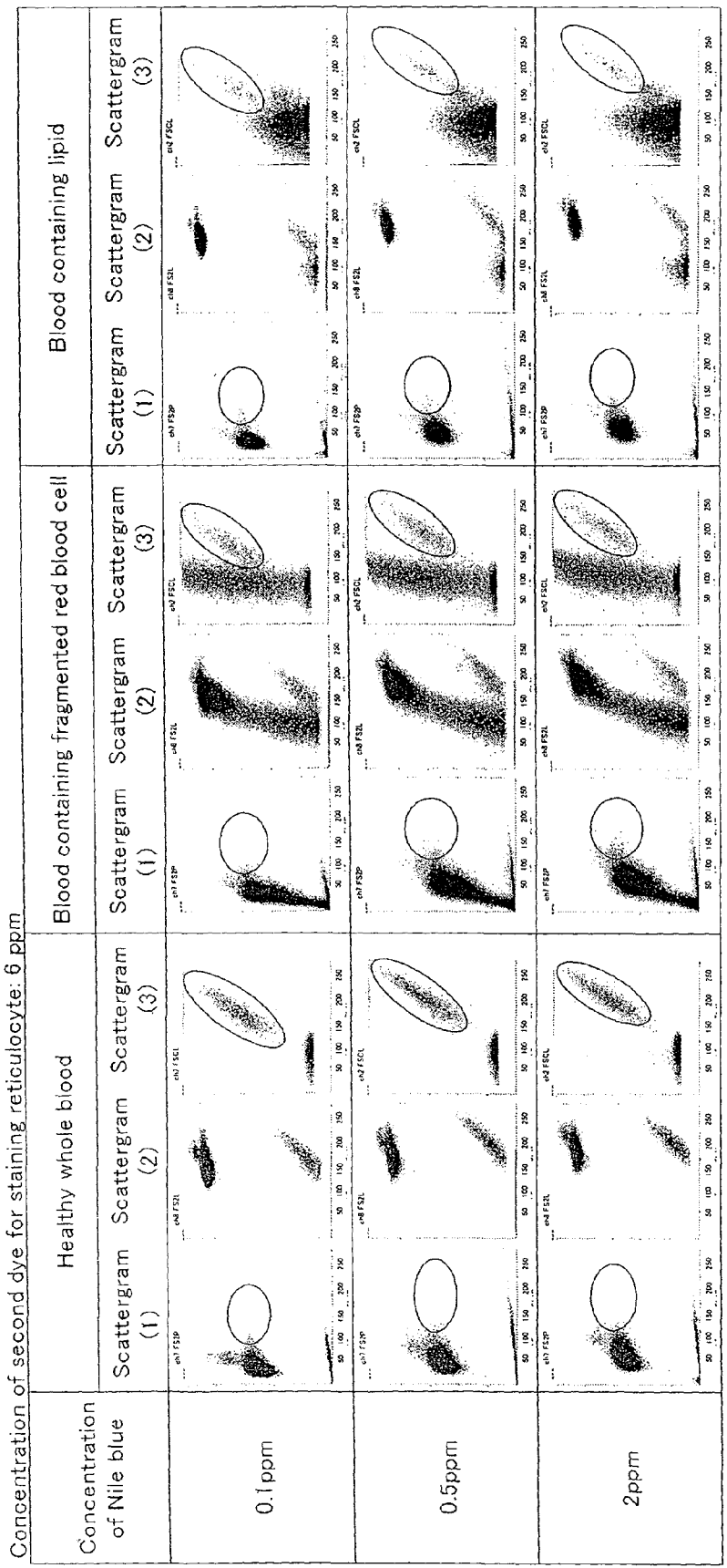
Figure 8C:
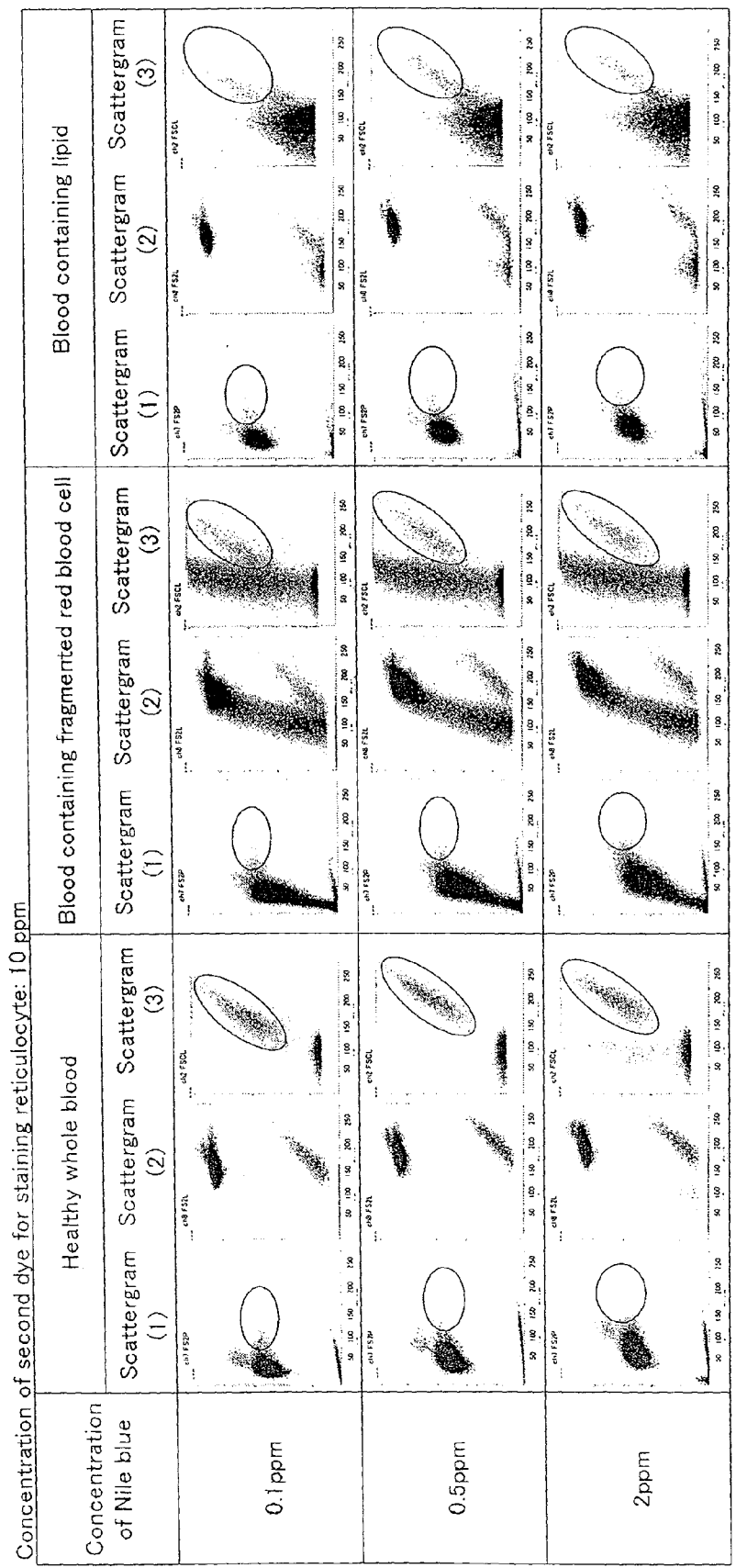

The resultant scattergrams are shown in FIGS. 8A, 8B and 8C. Scattergram (1) shows forward scattering light intensity on the ordinate and fluorescence intensity on the abscissa. Scattergram (2) is the same as scattergram (1) except that the ordinate has been converted into log. Scattergram (3) is an enlargement of an area including and around the region where platelets appear in scattergram (2). In scattergram (19, the region where reticulocytes appear is shown in solid line. In scattergram (3), the region where platelets appear is shown in solid line. From this result, it was found that when the concentration of the second dye is 0.5 ppm to 10 ppm and Nile blue chloride is 0.5 to 2.0 ppm, reticulocytes and platelets can be clearly distinguished from contaminants even if lipid and fragmented red blood cells occur as contaminants.

Example 11

In this example, the second dye for staining reticulocyte used in Example 8 was contained in the dye solution in Example 8. The second dye was contained in the dye solution such that the final concentration of the second dye became 0.5 ppm, 6 ppm or 10 ppm when the reagent was mixed with a sample. Brilliant cresyl blue ALD was also contained as the first dye for staining platelet in this dye solution. Brilliant cresyl blue ALD was contained in the dye solution such that the final concentration of brilliant cresyl blue ALD became 1 ppm, 1.5 ppm or 2 ppm when the reagent was mixed with a sample. The sample used was the same as in Example 8. Measurement was carried out in the same manner as in Example 8.

(Results)

Figure 9A:
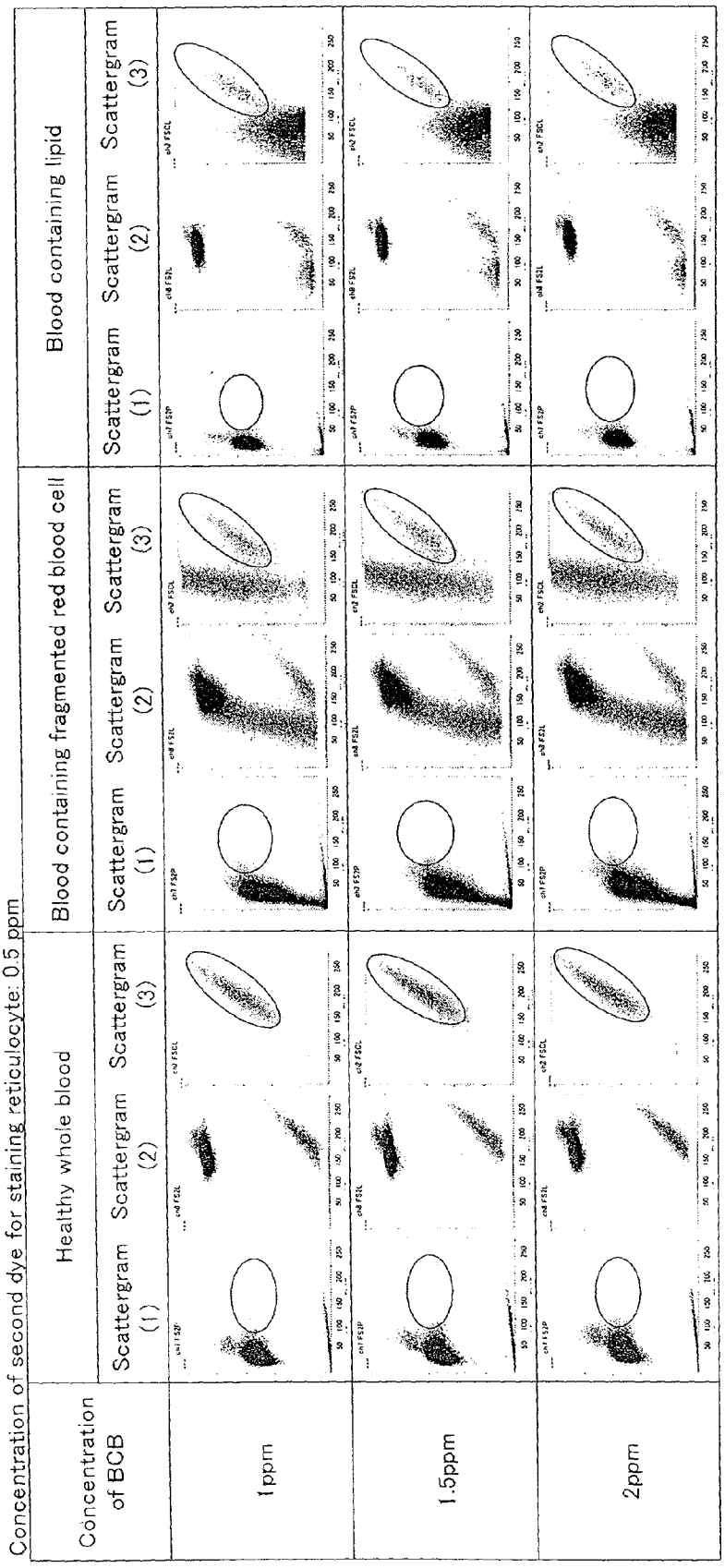
FIGS. 9A to C show scattergrams obtained by measurement using each reagent for analyzing reticulocyte and platelet with different concentrations of a dye for staining reticulocyte and different concentrations of a dye (brilliant cresyl blue) for staining platelet.
Figure 9B:
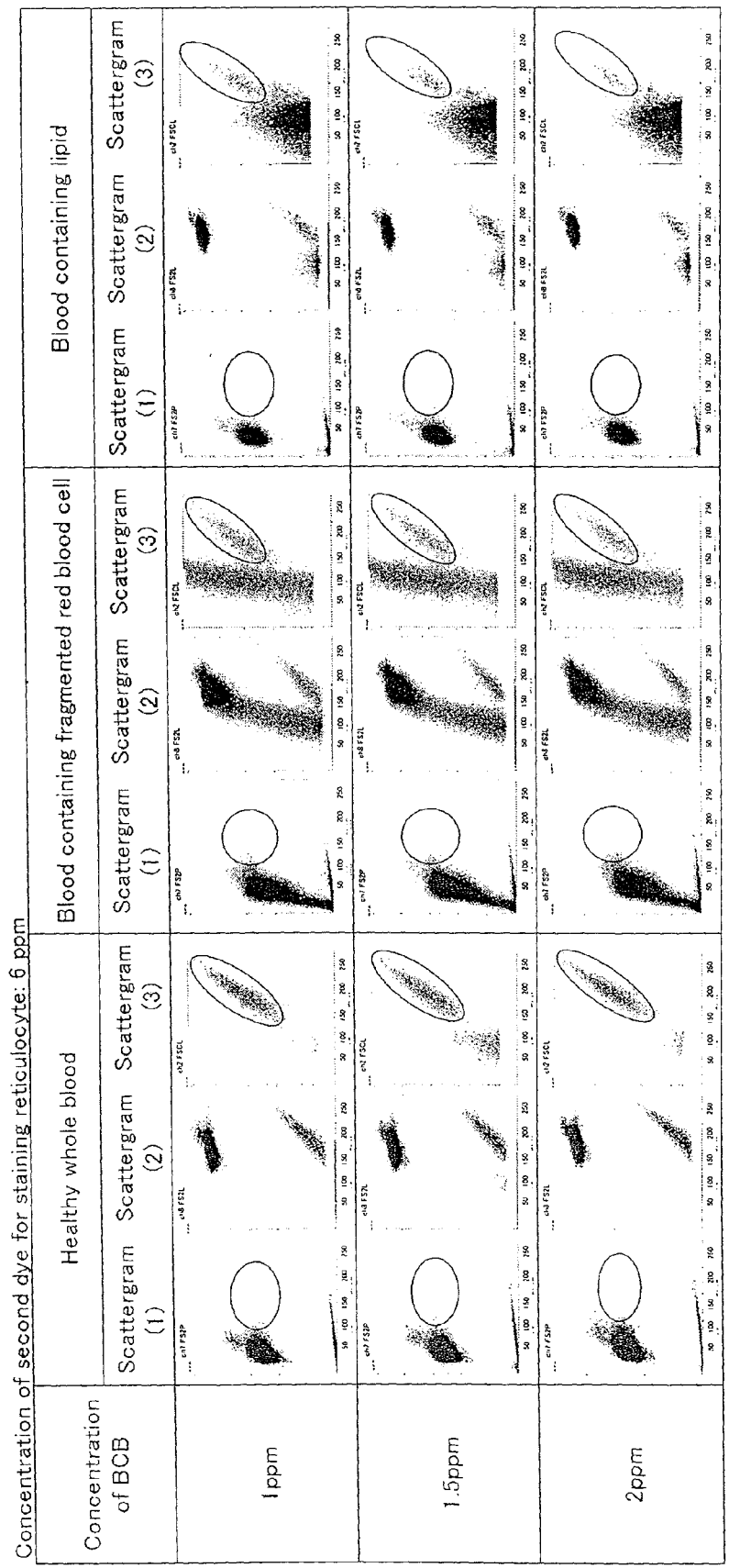
Figure 9C:
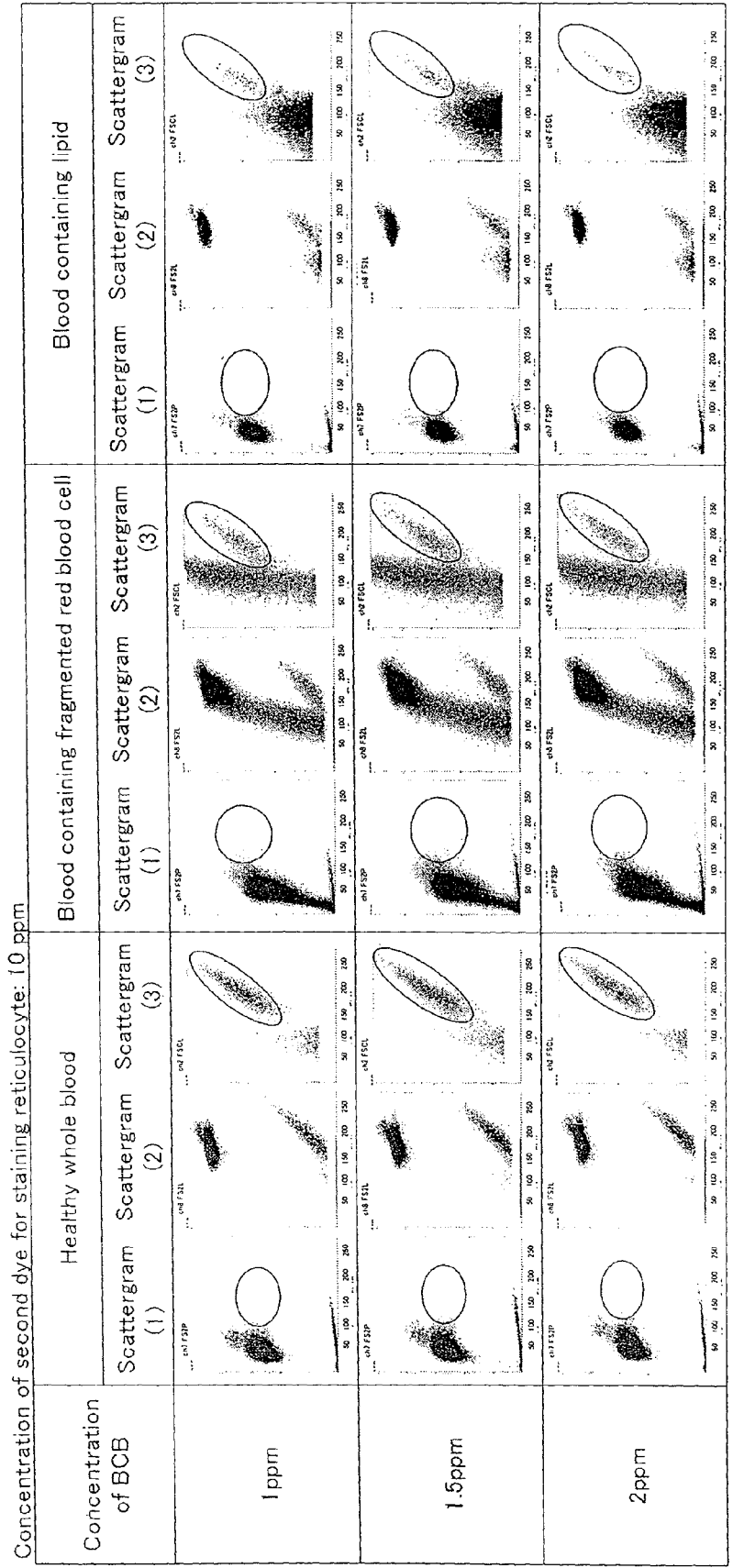

The resultant scattergrams are shown in FIGS. 9A, 9B and 9C. In these scattergrams, "BCB" refers to brilliant cresyl blue ALD. Scattergram (1) shows forward scattering light intensity on the ordinate and fluorescence intensity on the abscissa. Scattergram (2) is the same as scattergram (1) except that the ordinate has been converted into log. Scattergram (3) is an enlargement of an area including and around the region where platelets appear in scattergram (2). In scattergram (1), the region where reticulocytes appear is shown in solid line. In scattergram (3), the region where platelets appear is shown in solid line. From this result, it was found that when the concentration of the second dye is 0.5 ppm to 10 ppm and brilliant cresyl blue ALD is 1.0 to 2.0 ppm, reticulocytes and platelets can be clearly distinguished from contaminants even if lipid and fragmented red blood cell occur as contaminants.

What is claimed is:

1. A method for analyzing platelet, comprising the steps of:
    preparing a measurement sample by mixing a whole blood sample and Nile blue as a dye for staining platelet;
    measuring scattered light and fluorescence emitted from blood cells in the measurement sample by irradiating the blood cells with light; and
    detecting platelet by distinguishing platelet from other blood cells in the measurement sample on the basis of the scattered light and the fluorescence.

2. The method according to claim 1, wherein the preparing step comprises mixing the whole blood sample with a dye solution comprising the dye and a diluent comprising a buffer.

3. The method according to claim 2, wherein the diluent comprises a staining promoter for promoting penetration of the dye.

4. The method according to claim 3, wherein the staining promoter is a cationic surfactant.

5. The method according to claim 1, wherein the measuring step comprises steps of:
    introducing the measurement sample into a flow cell of a flow cytometer; and irradiating the blood cells in the flow cell with light.

6. The method according to claim 1, wherein the cells are irradiated with light of 600 to 680 nm wavelength.

7. The method according to claim 1, further comprising a step of counting the detected platelet.

8. The method according to claim 1, further comprising steps of:
    preparing a scattergram based on the detected scattered light and fluorescence; and displaying the prepared scattergram.

* * * * *